US012770729B2

(12) United States Patent
Ziemba et al.

(10) Patent No.: US 12,770,729 B2
(45) Date of Patent: Oct. 20, 2026

(54) VIRTUAL REALITY SIMULATION GENERATION AND RENDERING FOR SUBSTANCE USE DISORDER HEALTHCARE TREATMENT

(71) Applicant: InnateVR, LLC, Lake Orion, MI (US)

(72) Inventors: Jacob Ziemba, Lake Orion, MI (US); Paul Ziemba, Lake Orion, MI (US)

(73) Assignee: InnateVR, LLC, Lake Orion, MI (US)

(*) Notice: Subject to any disclaimer, the term of this patent is extended or adjusted under 35 U.S.C. 154(b) by 183 days.

(21) Appl. No.: 18/166,759

(22) Filed: Feb. 9, 2023

(65) Prior Publication Data

US 2024/0274267 A1 Aug. 15, 2024

(51) Int. Cl.

*G16H 20/70* (2018.01)
*G02B 27/01* (2006.01)
(Continued)

(52) U.S. Cl.

CPC ........... *G16H 20/70* (2018.01); *G02B 27/017* (2013.01); *G06T 19/006* (2013.01); *G16H 10/20* (2018.01); *G16H 40/67* (2018.01); *G16H 50/20* (2018.01)

(58) Field of Classification Search

CPC ........ G16H 20/70; G16H 10/20; G16H 40/67; G16H 50/20; G16H 20/10; G16H 40/63;
(Continued)

(56) References Cited

U.S. PATENT DOCUMENTS

2009/0164917 A1* 6/2009 Kelly ...................... G06F 3/011 715/757
2018/0176727 A1* 6/2018 Williams ............. A61B 5/6802
(Continued)

FOREIGN PATENT DOCUMENTS

| | | | | | |
|---|---|---|---|---|---|
| CA | 2889367 | C | * 12/2019 | ............... | G09B 9/02 |
| DE | 20 2019 105341 | U1 | 1/2021 | | |
| EP | 4016539 | A1 | 6/2022 | | |

OTHER PUBLICATIONS

Caponnetto et al., Update on Cyber Health Psychology: Virtual Reality and Mobile Health Tools in Psychotherapy, Clinical Rehabilitation, and Addiction Treatment, Mar. 16, 2022, International Journal of Environmental Research and Public Health, pp. 1-12. (Year: 2022).*

Mazza et al., Virtual reality: a powerful technology to provide novel insight into treatment mechanisms of addiction, Dec. 6, 2021, Translational Psychiatry, pp. 1-11. (Year: 2021).*

(Continued)

*Primary Examiner* — Christopher L Gilligan

(74) *Attorney, Agent, or Firm* — Young Basile Hanlon & MacFarlane, P.C.

(57) ABSTRACT

A virtual reality substance abuse treatment simulation is generated using input specific to a patient. The input indicates a type of substance used by the patient and one or more triggers for inducing substance use of that type of substance by the patient. At a computing device with which a virtual reality headset worn by the patient is in communication, instructions for running the virtual reality substance abuse treatment simulation are executed. Stimuli content associated with the type of substance and the one or more triggers are rendered as output for display at the virtual reality headset. Data indicative of exposures of the patient to ones of the stimuli content during the virtual reality substance abuse treatment simulation are transmitted to a remote device. Accordingly, a patient using the virtual reality substance abuse treatment simulation may experience a customized simulation tailored to their needs.

20 Claims, 15 Drawing Sheets

(51) Int. Cl.
*G06T 19/00* (2011.01)
*G16H 10/20* (2018.01)
*G16H 40/67* (2018.01)
*G16H 50/20* (2018.01)

(58) Field of Classification Search
CPC ..... G02B 27/017; G06T 19/006; A61B 5/165; G06F 3/011; H04L 67/131
See application file for complete search history.

(56) References Cited

U.S. PATENT DOCUMENTS

| | | | | |
|---|---|---|---|---|
| 2021/0043011 | A1* | 2/2021 | Gates | G02B 27/017 |
| 2023/0211205 | A1* | 7/2023 | Fung | A61B 5/375<br>710/1 |
| 2023/0386115 | A1* | 11/2023 | Oberlin | G06T 13/40 |
| 2024/0004470 | A1* | 1/2024 | Van Dooren | G16H 20/70 |
| 2024/0197652 | A1* | 6/2024 | Morgan | A61K 47/10 |
| 2024/0424245 | A1* | 12/2024 | Guest | G16H 50/20 |

OTHER PUBLICATIONS

Hanshans Christian et al: "Virtual Therapeutics—Requirements to deliver value with virtual reality and biofeedback applications for alcohol addiction therapy", Current Directions in Biomedical Engineering, vol. 7, No. 2, Oct. 9, 2021 (Oct. 9, 2021) , pp. 81-84.

Mahmoudi-Nejad Athar: "Automated Personalized Exposure Therapy Based on Physiological Measures Using Experience-Driven Procedural Content Generation", Proceedings of the AAAT Conference on Artificial Intelligence and Interactive Digital Entertainment, vol. 17, No. 1, Oct. 4, 2021 (Oct. 4, 2021), pp. 232-235.

Segawa Tomoyuki et al: "Virtual Reality (VR) in Assessment and Treatment of Addictive Disorders: A Systematic Review", Frontiers in Neuroscience, vol. 13, Jan. 10, 2020 (Jan. 10, 2020), XP093194099, CH ISSN: 1662-4548, DOL: 10.3389/fnins.2019.01409 The whole document.

International Search Report PCT/US2024/014591, issued Sep. 10, 2024.

* cited by examiner

800

VIRTUAL REALITY SIMULATION GENERATION AND RENDERING FOR SUBSTANCE USE DISORDER HEALTHCARE TREATMENT

TECHNICAL FIELD

This disclosure relates to virtual reality simulation generation and rendering, and, more particularly, to generating and rendering virtual reality simulations for substance use disorder healthcare treatment specific to individual patients.

SUMMARY

Disclosed herein are, inter alia, implementations of systems and techniques for generating and rendering a virtual reality simulation for substance use disorder healthcare treatment.

One aspect of this disclosure is a method, which includes generating a virtual reality substance abuse treatment simulation using input specific to a patient, in which the input indicates a type of substance used by the patient and one or more triggers for inducing substance use and craving by the patient. Instructions for running the virtual reality substance abuse treatment simulation are executed at a computing device with which a virtual reality headset worn by the patient is in communication to cause stimuli content associated with the type of substance and the one or more triggers to render as output for display at the virtual reality headset. Data indicative of exposures of the patient to ones of the stimuli content during the virtual reality substance abuse treatment simulation are then transmitted to a remote device.

Another aspect of this disclosure is a device, which includes a memory and a processor configured to execute instructions stored in the memory to select a virtual reality substance abuse treatment simulation specific to a patient, execute instructions for running the virtual reality substance abuse treatment simulation to cause stimuli content associated with a type of substance and one or more triggers to render as output for display to the patient, and output data indicative of exposures of the patient to one of the stimuli content during the virtual reality substance abuse treatment simulation.

Yet another aspect of this disclosure is a system, which includes a remote device, a computing device, and a virtual reality headset. The remote device receives data indicative of exposures of a patient to one or more stimuli content during a virtual reality substance abuse treatment simulation. The computing device, which is in communication with the remote device, generates a virtual reality substance abuse treatment simulation using input specific to the patient, in which the input indicates a type of substance used by the patient and one or more triggers for inducing substance use by the patient. The virtual reality headset, which is in communication with the computing device, renders the virtual reality substance abuse treatment simulation including the one or more stimuli content associated with the type of substance and the one or more triggers.

DETAILED DESCRIPTION

Figure 1:
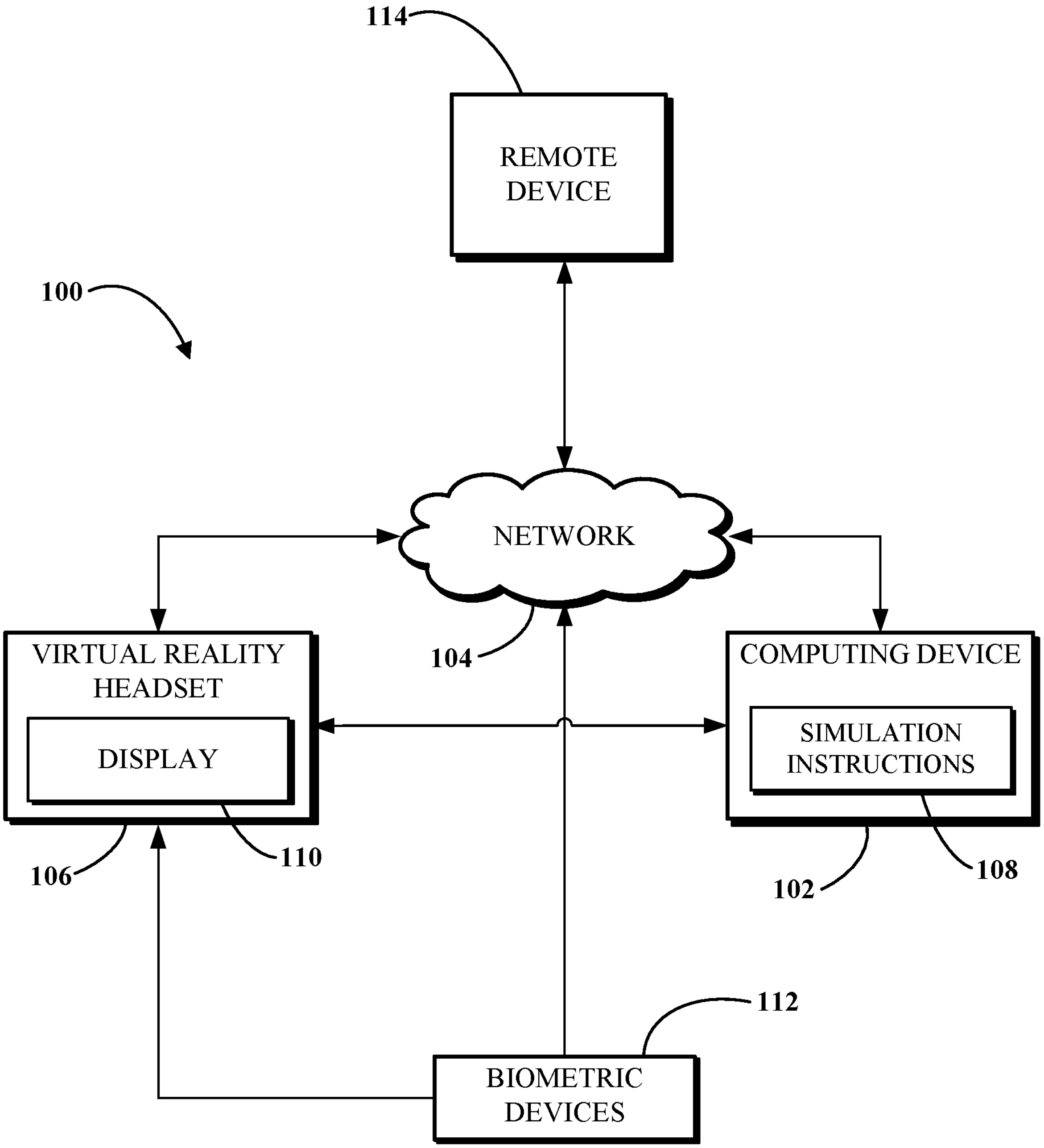
FIG. 1 is a block diagram of an example virtual reality platform.

Substance abuse is a chronic, recurring condition, which significantly impairs physical and psychological health and poses a substantial public health threat. Left untreated, a person suffering from substance abuse may inflict great bodily harm upon themselves or others, with potentially fatal results. Traditionally, there are a limited number of empirically supported behavioral treatments available for substance abuse intervention, including counseling and medication, which may not be accessible to all. To address the lack of available treatments, healthcare professionals have started using virtual reality to treat substance craving, one of the most salient components of substance abuse. Using a controlled virtual environment, patients are repeatedly exposed to substance use cues. Through repeated exposure, a patient's relationship between the craving and substance use cues weakens.

Given that each patient is unique, each patient's substance use cues and the many variables that trigger those cues are unique. As such, it is crucial that the virtual environment used for each individual patient be tailored to meet the unique circumstances of that patient. For example, some patients may be triggered into craving their substance of choice based on their proximity to certain specific people or objects, while others may be so triggered by being in certain specific environments. However, because of the technical challenges involved in programming and designing a virtual environment usable with a conventional virtual reality platform, such platforms lack the ability to customize the virtual environment quickly and easily to suit the unique needs of the patient. Instead, conventional virtual reality platforms provide a generic or generalized virtual environment that is not tailored to the individual experiences of the patient. A lack of customization of the virtual environment can lead to less patient engagement which may lead to ineffective treatment and premature termination of treatment.

Additionally, each environment needs to be able to evolve or change with a patient over time allowing the treatment of the patient to progress. In particular, during a course of treatment using a virtual environment rendered using a virtual reality platform, a patient suffering from substance abuse may make progress toward weakening their substance use cues. Over time, the patient's reactions to the specific cues represented within the virtual environment may decrease based on that progress, leading to limits on further gains realized in the treatment process. Without changing the virtual environment to align with the changes to the patient's progress, the treatment process using the virtual environment may stall, and, in some cases, lead to an undesirable substance use regression. However, given the lack of customizability with conventional virtual reality platforms, there are significant technical challenges to not only creating highly customized virtual environments specific to an individual patient's substance use cues, but also to updating such a highly customized virtual environment to account for progress in the substance abuse treatment process.

Implementations of this disclosure address problems such as these by generating and rendering virtual reality substance abuse treatment simulations for substance use disorder healthcare treatment specific to individual patients. The implementations of this disclosure allow for quick and easy customization of a virtual reality substance abuse treatment simulation for a patient both during the initial creation of the virtual environment and for subsequent sessions. These customizations are achieved through the use of software user interfaces which enable a user (e.g., the patient themselves or a healthcare professional associated with the patient) to specify configurations to use to generate a virtual reality substance abuse treatment simulation for an individual patient. The configurations may, for example, be specified using input gathered from or otherwise on behalf of the patient to indicate, amongst other things, a type of substance used by the patient and one or more triggers for inducing substance use of that type of substance by the patient. The configurations may be stored in an object notation format (e.g., JavaScript Object Notation (JSON)) and accessed by the software to generate the virtual reality substance abuse treatment simulation, for example, by producing instructions for running the virtual reality substance abuse treatment simulation.

The instructions for running the virtual reality substance abuse treatment simulation may thereafter be executed, such as at a virtual reality headset worn by the patient and used to render the virtual reality substance abuse treatment simulation or at a computing device in communication with that virtual reality headset. During the virtual reality substance abuse treatment simulation, stimuli content associated with the type of substance and the one or more triggers are rendered as output for display at the virtual reality headset. The patient is thus exposed at various times during the virtual reality substance abuse treatment simulation to the stimuli content. Data indicative of exposures of the patient to the stimuli content during the virtual reality substance abuse treatment simulation may thus output for use in updating the virtual reality substance abuse treatment simulation. Accordingly, a patient using a virtual reality substance abuse treatment simulation according to the implementations of this disclosure may experience a customized virtual reality substance abuse treatment simulation tailored to their specific needs, thereby substantially improving the chances of a successful treatment outcome.

To describe some implementations in greater detail, reference is first made to examples of hardware and software structures used to implement a system for customizing and displaying the virtual reality substance abuse treatment simulation. FIG. 1 is a block diagram of an example virtual reality platform 100, which can be or include a distributed computing system (e.g., a client-server computing system), a cloud computing system, a clustered computing system, or the like. The virtual reality platform 100 includes a computing device 102, which can, for example, be a computer having an internal configuration of hardware such as that described in FIG. 2. However, other implementations of the computing device 102 are possible. For example, the processing of the computing device 102 can be distributed among multiple devices. The computing device 102 executes instructions for running a virtual reality substance abuse treatment simulation for display to a patient. In some implementations, the virtual reality platform 100 may include multiple computing devices 102.

A network 104 can connect the computing device 102 and a virtual reality headset 106 worn by a patient and used for displaying the virtual reality substance abuse treatment simulation to a patient. Specifically, simulation instructions 108 for the virtual reality substance abuse treatment simulation may be executed at the computing device 102, in which the executed instructions may be sent, through the network 104, to the virtual reality headset 106 to render the virtual reality substance abuse treatment simulation at a display 110 of the virtual reality headset 106 for viewing by the patient. The network, 104 can be, for example, the Internet. The network can also be a local area network (LAN), wide area network (WAN), virtual private network (VPN), cellular telephone network, or another means of facilitating communications between the computing device 102 and the virtual reality headset 106. Alternatively, the virtual reality headset 106 may be in direct communication with the computing device 102 via a wired connection. In other such implementations the virtual reality headset 106 may include the computing device 102.

The virtual reality headset 106 may also be in communication with one or more biometric devices 112 that may be used to monitor, display, or both monitor and display real-time biometric information (e.g., heart rate, heart rate variation, or oxygen saturation about the patient during the virtual reality substance abuse treatment simulation, such as based on exposures of the patient to various stimuli content within the virtual reality substance abuse treatment simulation. For example, the biometric devices 112 may be or include one or more sensors for measuring human biometric information or one or more devices housing such sensors. The biometric devices 112 may be connected directly to the virtual reality headset 106 or, in some cases, connected through the network 104 to another device, such as the computing device 102 and/or the remote device 114 (described below). For example, the virtual reality headset 106 may have an internal biometric device for monitoring the wearers heart rate. As such, using the biometric devices 112, the virtual reality headset 106 may collect heart rate information and display it to the patient or a healthcare professional associated with the patient during the virtual reality substance abuse treatment simulation.

A remote device 114 may also be in communication with the virtual reality headset 106 and/or the computing device 102 via the network 104. The remote device 114 may, for example, be a smartphone, a tablet, a laptop computer, a desktop computer, or a server computer. The remote device 114 may receive data related to the running of the virtual reality substance abuse treatment simulation. For example, the remote device 112 may receive data indicative of exposures of the patient wearing the virtual reality headset 106 to stimuli content within the virtual reality substance abuse treatment simulation during the virtual reality substance abuse treatment simulation. In at least some such cases, the data may be expressed as or otherwise based on the biometric information measured using the biometric devices 112. In some implementations, the computing device 102 may receive data related to the running of the virtual reality substance abuse treatment simulation. In some such implementations, the remote device 114 may be omitted.

The virtual reality platform 100 can be used to run a virtual reality substance abuse treatment simulation for a patient using the virtual reality headset 106. In an example, the virtual reality headset 106 may be connected to the computing device 102 which is of a healthcare professional associated with the patient. The healthcare professional selects the virtual reality substance abuse treatment simulation to run (e.g., using the GUI of FIG. 6A, described below). The healthcare professional indicates to the computing device 102 to cause the simulation instructions 108 to be executed by the computing device 102. In executing the simulation instructions 108, the computing device causes the virtual reality substance abuse treatment simulation to render at the display 110 of the virtual reality headset 106 while same is worn by the patient. The biometrics devices 112 receive biometrics readings (e.g., exposure indication data, as described below with respect to FIG. 3) as the patient interacts with the virtual reality substance abuse treatment simulation. The biometrics readings are transmitted to the virtual reality headset 106, the computing device 102 and/or the remote device 108 via the network 104. The virtual reality headset 106, the computing device 102, and/or the remote device 108 may in some cases display the biometric readings to the patient and/or the healthcare professional in real-time. The biometrics readings are stored in connection with the patient and the virtual reality substance abuse treatment simulation and may be later used to update or otherwise determine recommendations for updating the virtual reality substance abuse treatment simulation.

Figure 2:
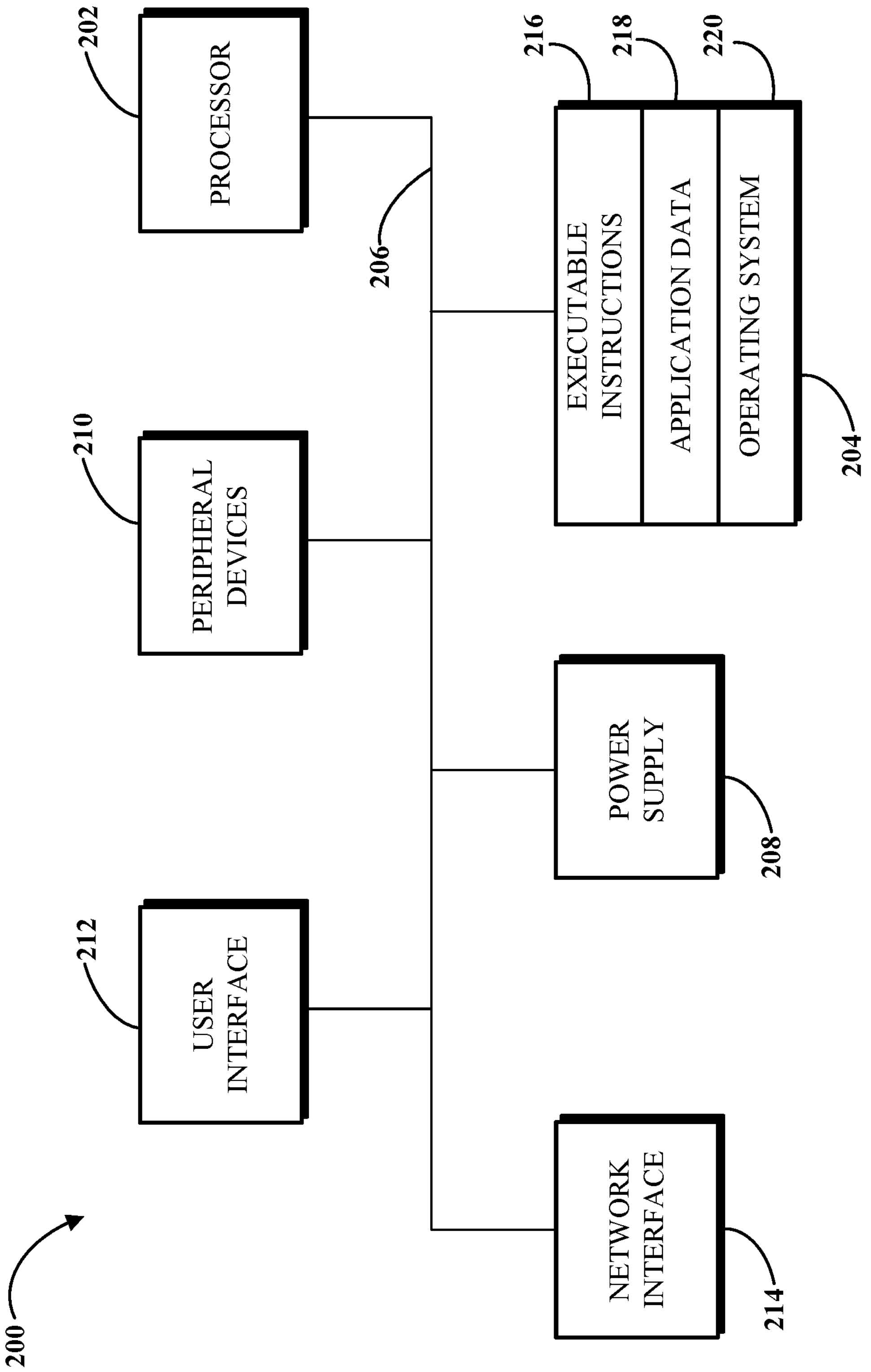
FIG. 2 is a block diagram of an example internal configuration of a computing device of a virtual reality platform.

FIG. 2 is a block diagram of an example internal configuration of a computing device 200 of a virtual reality platform. In one configuration, the computing device 200 may be the computing device 102, virtual reality headset 106, or the remote device 114 shown in FIG. 1.

The computing device 200 includes components or units, such as a processor 202, a memory 204, a bus 206, a power supply 208, peripheral devices 210, a user interface 212, a network interface 214, other suitable components, or a combination thereof. One or more of the memory 204, the power supply 208, the peripheral devices 210, the user interface 212, or the network interface 214 can communicate with the processor 202 via the bus 206.

The processor 202 is a central processing unit (CPU), such as a microprocessor, and can include single or multiple processors having single or multiple processing cores. Alternatively, the processor 202 can include another type of device, or multiple devices, configured for manipulating or processing information. For example, the processor 202 can include multiple processors interconnected in one or more manners, including hardwired or networked, including wirelessly networked. The operations of the processor 202 can be distributed across multiple devices or units that can be coupled directly or across a local area or other suitable type of network. The processor 202 can include a cache, or cache memory, for local storage of operating data or instructions.

The memory 204 includes one or more memory components, which may each be volatile memory, such as random access memory (RAM) (e.g., a DRAM module, such as DDR SDRAM), or non-volatile memory, such as a disk drive, a solid state drive, flash memory, or phase-change memory, or any other form of non-volatile memory. In some implementations, the memory 204 can be distributed across multiple devices. For example, the memory 204 can include network attached storage (NAS) or other network-based memory or memory in multiple clients or servers performing the operations of those multiple devices. The memory 204 can include data for immediate access by the processor 202. For example, the memory 204 can include executable instructions 216, application data 218, and an operating system 220.

Although shown here as a single block, the memory 204 can be implemented as multiple units. For example, a computing device 200 can include persistent memory, such as hard disk drive (HDD) or solid-state drive (SSD), NAS, and volatile memory, such as DRAM or DDR SDRAM. The memory can be distributed across multiple clients or servers, such as network-based memory or memory in multiple clients or servers performing the operations of client or servers.

The executable instructions 216 can include one or more application programs, which can be loaded or copied, in whole or in part, from non-volatile memory to volatile memory to be executed by the processor 202. For example, the executable instructions 216 can include instructions for performing some or all of the techniques of this disclosure. The application data 218 can include user data, file data (e.g., system files, application files, or user files), database data (e.g., database catalogs or dictionaries), or the like. In some implementations, the application data 218 can include functional programs, such as a web browser, a web server, a database server, another program, or a combination thereof. The operating system 220 can be, for example, Microsoft Windows®, Mac OS X®, Linux®, ChromeOS®, Android®, iOS® or any other operating system for but not limited to personal computers, mainframe computer, or mobiles device, such as a smartphone or tablet devices.

The power supply 208 provides power to the computing device 200. For example, the power supply 208 can be an interface to an external power distribution system. In another example, the power supply 208 can be a battery, such as where the computing device 200 is a mobile device or is otherwise configured to operate independently of an external power distribution system. In some implementations, the computing device 200 may include or otherwise use multiple power sources. In some such implementations, the power supply 208 can be a backup battery.

The peripheral devices 210 includes one or more sensors, detectors, or other devices configured for monitoring the computing device 200 or the environment around the computing device 200. The peripheral devices 210 can be internal components connected to the computing device 200 via the bus 206 or external components connected to the computing device 200 indirectly through the network interface 214. For example, the peripheral devices 210 can include a geolocation component, such as a global positioning system location unit. In another example, the peripheral devices can include a temperature sensor for measuring temperatures of components of the computing device 200, such as the processor 202. In a further example, the peripheral devices can include a heartrate monitor for measure the heartrate from an external source. In some implementations, the computing device 200 can omit the peripheral devices 210.

The user interface 212 includes one or more input interfaces and/or output interfaces. An input interface may, for example, be a positional input device, such as a mouse, touchpad, touchscreen, or the like; a keyboard; or another suitable human or machine interface device. An output interface may, for example, be a display, such as a liquid crystal display, a cathode-ray tube, a light emitting diode display, or other suitable display.

Figure 3:
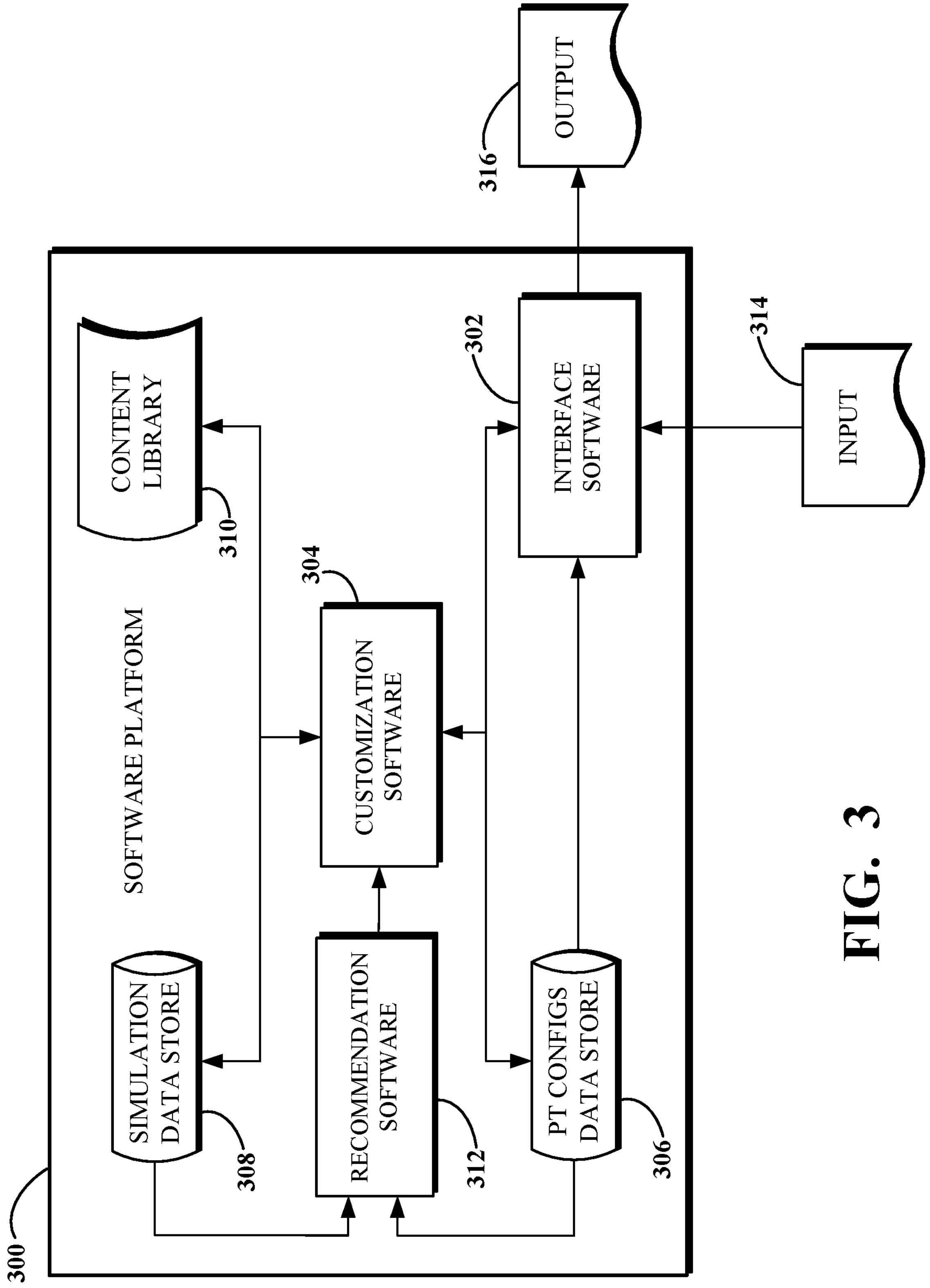
FIG. 3 is a block diagram of an example of a software platform for implementing a virtual reality platform for generating and running a virtual reality substance abuse treatment simulation.

The network interface 214 provides a connection or link to a network (e.g., the network 104 shown in FIG. 1). The network interface 214 can be a wired network interface or a wireless network interface. The computing device 200 can communicate with other devices via the network interface 214 using one or more network protocols, such as using Ethernet, transmission control protocol (TCP), internet protocol (IP), power line communication, an IEEE 802.X protocol (e.g., Wi-Fi, Bluetooth, or ZigBee), infrared, visible light, general packet radio service (GPRS), global system for mobile communications (GSM), code-division multiple access (CDMA), Z-Wave, another protocol, or a combination thereof FIG. 3 is a block diagram of an example of a software platform 300 for implementing a virtual reality platform for generating and running a virtual reality substance abuse treatment simulation, such as the virtual reality platform 100 shown in FIG. 1. The software platform 300 can be accessed using the computing device 102, the virtual reality headset 106, the remote device 114, or the like, or a combination thereof. The software platform 300 may, for example, be a multi-tenant platform instantiated using one of more computing devices 102, virtual reality headsets 106, remote devices 112, or the like as shown in FIG. 1.

The software platform 300 includes software services accessible via interface software 302. For example, a computing device 102 may send and receive data from the software platform using the network 104 to connect to the interface software 302. The interface software 302 is software used by the software platform 300 to interface with other devices or applications and thus enables the software platform 300 to communicate with such other devices or applications, for example, using a software development kit (SDK), application programming interface (API), or the like. The SDK may, for example, be implemented in any programming language such as Java, C, C++, JavaScript, C#, or the like. The API may, for example, be implemented using a representational state transfer (ReST) architecture, simple object access protocol (SOAP), or the like.

The software platform includes customization software 304. The customization software 304 is accessed using the interface software 302. The customization software 304 generates a virtual reality substance abuse treatment simulation for a patient. In particular, the customization software 304 generates information (e.g., instructions) usable (e.g., executable) to run the virtual reality substance abuse treatment simulation. The information may be or otherwise represent patient configurations and simulation data. The patient configurations may be generated by the customization software 304 using patient-specific data received at the software platform 300 (e.g., as the input 314, described below). For example, the customization software 304 may generate the patient configurations using responses to a questionnaire addressing a subject patient's specific substance abuse history, cues, and/or traumas. The simulation data may be generated by the customization software 304 based on the patient-specific data and/or other data usable to build a virtual reality substance abuse treatment simulation. For example, the customization software 304 may generate the simulation data based on the patient configurations and/or a framework for modeling virtual reality substance abuse treatment simulations. In some cases, the simulation data may include all the information pertaining to every customization, virtual environment, patient, and virtual reality substance abuse treatment simulation generated using the software platform 300. In such a case, the patient configurations may be specific to a patient while the simulation data may not be.

The customization software 304 may store the virtual reality substance abuse treatment simulation (e.g., as the information generated specifically for a subject patient) in a patient configurations data store 306 as well as a simulation data store 308. The patient configurations data store 306 stores a description of or a set of files describing the patient configurations generated for an individual patient. For example, the patient configurations data store 306 may store the patient configurations as files containing instructions in JSON, eXtensible Markup Language (XML), or the like. The simulation data store 308 stores a description or set of files describing the simulation data generated for the individual patient. For example, the simulation data store 308 may store the simulation data as files containing instructions in Structured Query Language (SQL), JSON, or the like. The patient configurations data store 306 and the simulation data store 308 may each, for example, be a relational database (e.g., implemented using a relational database management system (RDBMS)), a non-relational database (e.g., implemented using NoSQL), a document database, an object-oriented database, a key-value store, or the like.

To generate the simulation data, the customization software 304 obtains content from a content library 310. The content library 310 is a library which contains individual assets available for placement within one or more locations of a virtual reality substance abuse treatment simulation. The assets included in the content library 310 may be two-dimensional images or three-dimensional models stored in one or more various file formats, or they may be instructions usable to render such an image or model. The assets of the content library 310 may be added to the content library 310 by an administrator, developer, or like user of the software platform 300. In some cases, one or more of the assets may be added by a patient or a healthcare professional associated with a patient for whom a virtual reality substance abuse treatment simulation is generated. An individual asset may be a visual representation of a familiar place or setting for a patient, an avatar representing an individual that the patient is familiar with or a type of person (e.g., a doctor, drug dealer, or military officer) that the patient has a certain history with, an item that can be placed with or otherwise used to decorate the environment, or the like. For example, an asset within the content library 310 may represent the interior of a generic or particular model of a car, truck, or the like so as to facilitate a patient-specific virtual reality substance abuse treatment simulation for a particular patient who associates substance abuse with their vehicle. In such a case, the asset may be obtained from an external source (e.g., a vehicle manufacturer website) or produced (e.g., by a developer of the software platform 300) for general use by various patients. In another example, an asset within the content library 310 may represent an avatar for a person of specific importance or relevance to a patient. In such a case, the asset may be generated (e.g., by modeling against a humanoid object template) using an image of the person uploaded by or on behalf of the patient.

At least some of the content from the content library 310 is used as stimuli content intended to provoke a response by a patient interacting with a virtual reality substance abuse treatment simulation. For example, the stimuli content may represent objects that are known (e.g., by the patient or a healthcare professional associated with the patient) to cause the patient to react in a manner consistent with substance use or the desire therefor. Examples of stimuli content include, but are not limited to, objects corresponding to a specific substance used by the patient (e.g., beer bottles, a pipe, a bong, needles, or the like), avatars of certain people or types of people, and objects related to past (e.g., prior) traumas suffered by the patient (e.g., guns, belts, troubling images, or the like). The response intended to be provoked by the patient based on their exposure to the stimuli content may be measured in terms of biometric output, for example, using the biometric device 112 shown in FIG. 1.

The customization software 304 may allow a user to select a virtual environment from the content library 310 to be used as the traversable environment of the virtual reality substance abuse treatment simulation. The virtual environment may include one or more areas, each representing a geographical location, a place, a room, or the like. The patient, healthcare professional, or other user of the software platform 300 may select those one or more areas from the content library 310 to be used as the virtual environment. In at least some cases, the patient, healthcare professional, or other user may specify locations of the various areas with respect to one another within the virtual environment, so as to more closely design the virtual environment according to the specific patient for whom the virtual reality substance abuse treatment simulation is generated.

To illustrate an example use case of the software platform 300, when a patient fills out the questionnaire, the selections made by the patient are set as array variables. The array variables are then serialized into JSON array fields. The questionnaire data, in JSON format, is sent via the network, and received by the computing device. Next, on the computing device the JSON data is deserialized, JSON array fields are parsed as array variables, and the array variables are set in a high-level manager object for use within an instance of the patient's virtual environment at runtime. When the simulation is started, the variables are accessed via the manager object and used to customize the virtual environment.

In this example, the virtual reality substance abuse treatment simulation is a precompiled program that uses the data associated with a patient during runtime to customize the program. When the healthcare professional selects an environment from the menu item in the GUI and the virtual reality substance abuse treatment simulation is started, the environment selected by the healthcare professional is retrieved and that environment is loaded. When the environment is loaded, the array variables (e.g., substance cues, avatars, and behavior animations) are retrieved from the high-level manager object. By default, the available substance cues have already been placed in multiple zones in the virtual environment and have their visibility set to false. The substance cues that are in the array variables then have their visibility set to true. The avatars with their substance use behavior animations (e.g., inject, smoke, snort, neutral) are spawned in pre-defined locations in the environment. The avatars that are spawned for each substance use behavior animation are determined by the avatar array variables. If multiple avatars are available with the array variables for a substance use behavior animation, then a random avatar is selected from the array variables for that substance use behavior animation. The randomly selected avatar is then spawned into the environment for the corresponding substance use behavior animation. As such, different avatars and substance use behavior animations can be spawned each time the simulation is loaded. For example, if the patient selected one avatar for the inject substance use behavior animation and three avatars for the smoke substance use behavior animation, then when the virtual reality substance abuse treatment simulation is started one avatar for the inject substance use behavior animation and one of the three avatars, based on a random selection, for the smoke substance use behavior will be spawned. The healthcare professional can then manually control when the substance use behavior animations and dialog for the avatars are executed, or have the substance use behavior animations automatically execute after a certain amount of time.

The interface software 302 may receive input 314 from external sources, which the customization software 304 uses in various ways with the software services of the software platform 300. The input 314 can be received from one or more external sources at one or more times (e.g., relative to the generation and/or running of a virtual reality substance abuse treatment simulation) and may be represented in different forms. For example, the input 314 may be or otherwise correspond to responses to a questionnaire implemented via a web form or other format. The questionnaire may prompt the user viewing the questionnaire for data about a patient's past substance abuse or trauma associated with substance abuse. In some implementations, the questionnaire may be a physical form hand-written by a patient and input into the interface software 302 by a healthcare professional. Alternatively, the questionnaire may be a web-based form that is submitted directly into the interface software 302. In such a case, the interface software 302 stores the input 314 in the patient configurations data store 306.

In another example, the input 314 may be or otherwise correspond to exposure indication data. The exposure indication data indicates exposures of the patient to ones of the stimuli content within the virtual reality substance abuse treatment simulation. The input 314 including exposure indication data may be received from a patient using the biometric device 112 shown in FIG. 1. For example, during a patient's treatment using a virtual reality substance abuse treatment simulation, the patient may be wearing a biometric device to monitor the patient's heart rate. The data output by the biometric device based on the patient's interactions within the virtual reality substance abuse treatment simulation (e.g., based on exposures of the patient to various stimuli content therein) may be transmitted to the virtual reality headset 106, the remote device 114, and/or the computing device 102. The virtual reality headset 106, the remote device 114, and/or the computing device 102 may then transmit that data to the interface software 302. The exposure indication data may in some cases be stored by the interface software 302, for example, in the simulation data store 308.

The software platform 300 further includes recommendation software 312 for recommending changes to a virtual reality substance abuse treatment simulation based on a patient's experiences therewith. The recommendation software 312 analyzes the input 314 (e.g., as the exposure indication data) received from the interface software 302 combined with the data stored in the simulation data store 308 and the patient configurations data store 306 to determine one or more changes to recommend. Examples of changes may include relocating certain content within the virtual environment of the virtual reality substance abuse treatment simulation, replacing certain of the content based on the existing content having too profound or too insignificant an effect (e.g., an intensity) on the patient (e.g., as measured based on the exposure indication data), or adding or removing certain content to or from the virtual reality substance abuse treatment simulation. The recommendation software 312 may, for example, use the analysis of the various data to provide recommendations to a healthcare professional about how to further customize the virtual reality substance abuse treatment simulation to provide optimized results for the patient. The recommendation software 312 may in some cases use a machine learning model to perform the analysis. The machine learning model may, for example, be trained to evaluate biometric measurements included in exposure indication data for the patient against expected measurements (e.g., thresholds) according to biometric baselines for the patient individually or across a group of patients in the aggregate. For example, the recommendation software 312 may be configured with a machine learning model to analyze and predict the patient's heart rate during a virtual reality substance abuse treatment simulation. If the patient's actual heart rate is lower than the predicted heart rate the recommendation software 312 might recommend adjusting the virtual reality substance abuse treatment stimulation to provide more stimulation to the patient. Alternatively, the recommendation software 312 could be implemented using a rules-based module to achieve the same or a similar outcome.

The software platform, through the interface software 302 may also generate output 316. Output 316 may come in a variety of forms. The output 316 may be a list of patients with configurations stored in the patient configurations data store 306, or a list of environments, areas, or other assets (e.g. avatars, object, etc.) from the content library. Additionally, the output 316 may be any other data stored within the patient configurations data store 306, the simulation data store 308 or both. Alternatively, the output 316 may be a set of instructions for executing a virtual reality substance abuse treatment simulation. As a further alternative, the output 316 may include recommendations for changing (e.g., modifying) the virtual reality substance abuse treatment simulation.

Figure 4:
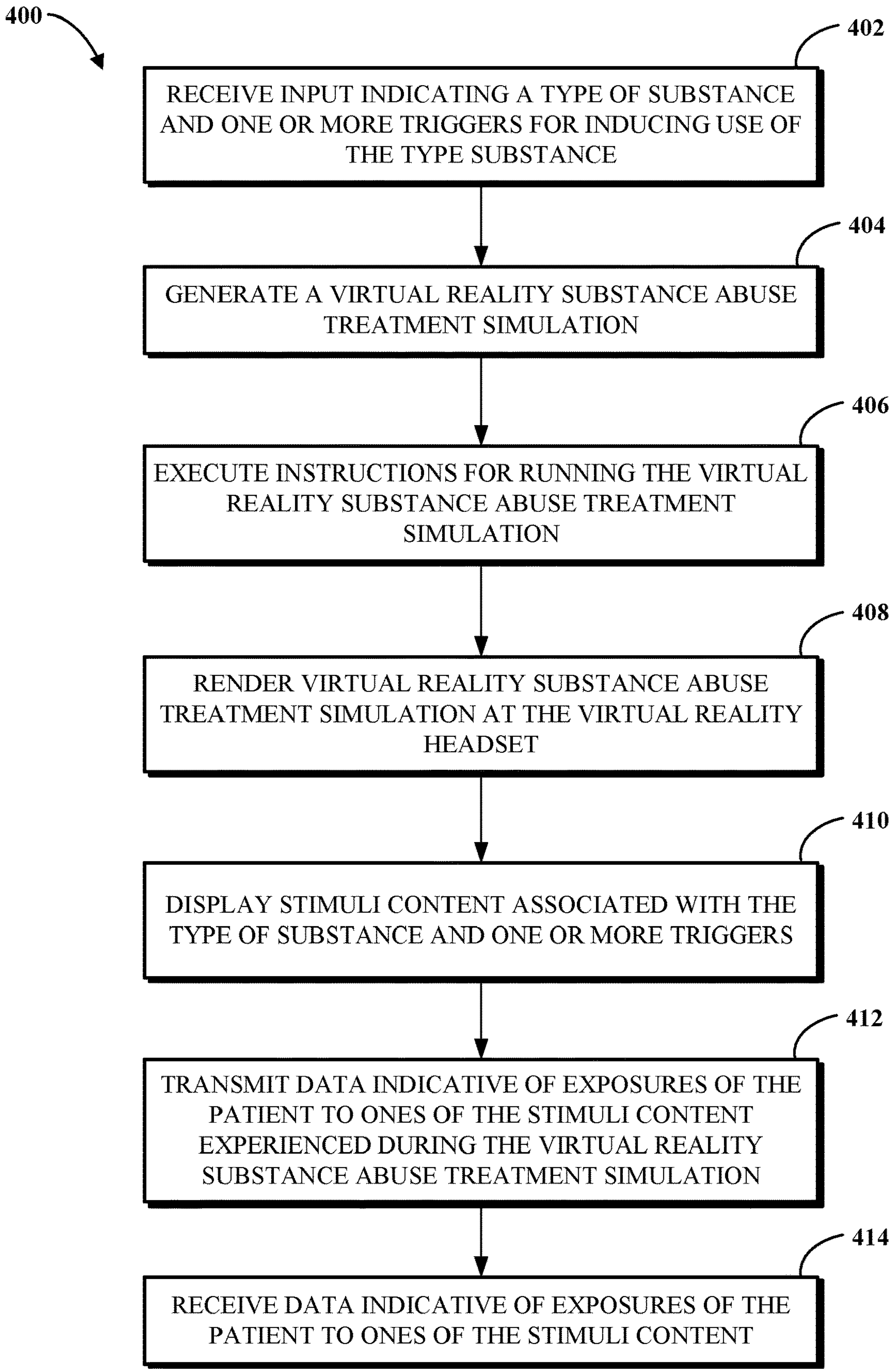
FIG. 4 is a flowchart of an example of a technique for generating a virtual reality substance abuse treatment simulation.
Figure 5:
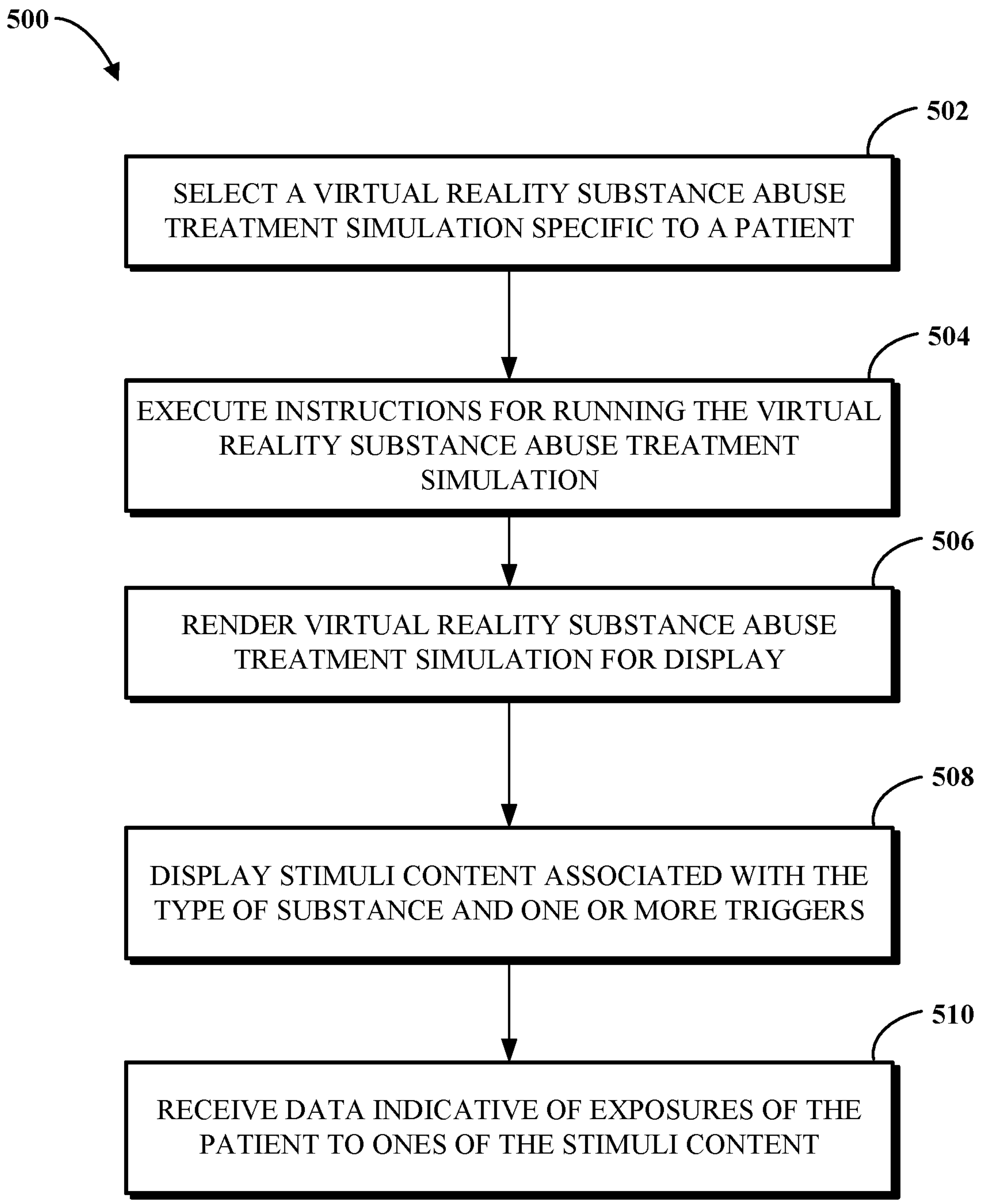
FIG. 5 is a flowchart diagram of an example of a technique for rendering a virtual reality substance abuse treatment simulation.

Further details of techniques for generating and rendering a virtual reality substance abuse treatment simulation are now described. FIG. 4 is a flowchart of an example of a technique 400 for generating a virtual reality substance abuse treatment simulation. FIG. 5 is a flowchart diagram of an example of a technique 500 for rendering a virtual reality substance abuse treatment simulation.

The technique 400, and/or the technique 500 can be implemented, for example, as a software program that may be executed by a computing device 102 or the virtual reality headset 106. For example, the software program can include machine-readable instructions that may be stored in a memory such as the memory 204, and that, when executed by a processor, such as the processor 202, may cause the computing device 102 or the virtual reality headset 106 to perform the technique 400 and/or the technique 500. As explained above, some computing devices 102 may have multiple memories or processors, and the operations described in the technique 400 and/or the technique 500 can be distributed using multiple processors, memories, or both.

For simplicity of explanation, the technique 400 and the technique 500 are each depicted and described herein as a series of steps or operations. However, the steps or operations in accordance with this disclosure can occur in various orders and/or concurrently. Additionally, other steps or operations may be required to implement a technique in accordance with the disclosed subject matter.

Referring first to FIG. 4, the technique 400 for generating a virtual reality substance abuse treatment simulation is shown. At 402 input is received. The input may describe a type of substance as well as one or more triggers for inducing the use of the type of substance. The input may be entered by a user or from a webform representing a questionnaire used to solicit information about a patient's substance abuse history, a patient's trauma history or both.

At 404, a virtual reality substance abuse treatment simulation is generated using the input. The virtual reality substance abuse treatment simulation may be generated automatically based on the received input or the virtual reality substance abuse treatment simulation may be generated manually with further input. The generated virtual environment may then be stored in a data store such as the simulation data store 308 from FIG. 3.

At 406, instructions for running the virtual reality substance abuse treatment simulation are executed. The instructions may be executed on the computing device 102 or the virtual reality headset 106 of FIG. 1. Executing the instructions includes communicating with the software platform 300 through the interface software 302 of FIG. 3. The interface software 302 communicates with the customization software 304 to obtain the patient configurations for the relevant patient and virtual reality substance abuse treatment simulation, the data stored in simulation data store 308 relevant to the requested virtual reality substance abuse treatment simulation and the content from content library 310. Each patient may have one or more virtual reality substance abuse treatment simulation available, as such, part of the instructions to execute the virtual reality substance abuse treatment simulation will include inputs describing which virtual reality substance abuse treatment simulation to run and for which patient.

At 408, the virtual reality substance abuse treatment simulation is rendered at the virtual reality headset. The rendering of the virtual reality substance abuse treatment simulation may cause an environment to be loaded from the content library 310 of FIG. 3. The environment may be comprised of one or more areas within the environment, such as multiple rooms of a dwelling known to the patient or an establishment familiar to the patient or other environment familiar to the patient. The areas may also be obtained from the content library 310 of FIG. 3.

At 410, stimuli content associated with the type of substance and one or more triggers is displayed. The stimuli content may be facsimiles of any object that a patient associates with the type of substance such as but not limited to beer bottles, a pipe, a bong, needles, or the like. The image assets associated with the stimuli content may be stored within the content library 310 whereas the placement details of how and where content is located within the virtual reality substance abuse treatment simulation may be stored in the simulation data store 308, the patient configurations data store 306, or a combination of both.

At 412, data indicative of exposures of the patient to ones of the stimuli content experienced during the virtual reality substance abuse treatment simulation is transmitted. The data may be transmitted to the remote device 114 of FIG. 1. The data may represent physiological reactions of the patient to one or more of the stimuli content experienced during the virtual reality substance abuse treatment simulation. The biometric devices 112 of FIG. 1 may be used to collect the physiological reaction. For example, a patient may be wearing a heart rate monitor while the virtual reality substance abuse treatment simulation is running. The heart rate monitor may collect data indicating an increased heart rate then one or more of the stimuli content are rendered within the virtual reality substance abuse treatment simulation. The increased heart date may be captured and sent to the remote device 114, and/or the computing device 102 during the virtual reality substance abuse treatment simulation.

At 414, the data indicative of exposures of the patient to ones of the stimuli content is received. The data may be received by the remote device 114 and/or the computing device 102 of FIG. 1. The remote device 114 and/or the computing device 102 may then communicate this data to the virtual reality headset 106 or the computing device 102 of FIG. 1. The data may also be transmitted to the software platform 300 using the interface software 302. The interface software may then communicate the data to the customization software 304. The customization software 304 may store the data in the simulation data store 308 associated with the patient and virtual reality substance abuse treatment simulation. The recommendation software 312 may then use the data to make recommendations regarding the experience of the patient during the virtual reality substance abuse treatment simulation. The recommendation software 312 may use a machine learning module to analyze the data and determine if the virtual reality substance abuse treatment simulation should be further customized to provide an optimal experience for the patient.

In some implementations, the technique 400 may include generating the virtual reality substance abuse treatment simulation. For example, a patient may fill out a web-based questionnaire designed to gather input 314 about the past substance abuse or trauma associated with substance abuse of the patient. The input 314 is received by the software platform 300. The healthcare professional associated with the patient can interface with the customization software 304 to generate a customized virtual reality substance abuse treatment simulation. The simulation is generated based on the input 314 provided by the patient, content contained within the content library 310, and any other data the healthcare professional may have available. All the data associated with the virtual reality substance abuse treatment simulation is stored in the simulation data store 308, the patient configuration data store 306, or a combination of both. When the healthcare professional, using a computing device 102 executes the simulation instructions 108, the computing device will request the simulation data from the software platform 300 using the interface software 302. The software platform will obtain all the information required from the simulation data store 308, the patient configuration data store 306, and the content library 310 to generate a virtual reality substance abuse treatment simulation. The virtual reality substance abuse treatment simulation is sent via the network 104 to the display 110 of the virtual reality headset 106 worn by the patient. Alternatively, the virtual reality substance abuse treatment simulation may be sent to the display 110 of the virtual reality headset 106 via a direct wired connection.

Referring next to FIG. 5, the technique 500 for rendering a virtual reality substance abuse treatment simulation is shown. At 502, a virtual reality substance abuse treatment simulation is selected for a specific patient. The selection may be made using the computing device 102, the virtual reality headset 106 of the remote device 114 of FIG. 1. The selection may also be done in accordance the interfaces of FIGS. 6A-6E or FIGS. 7A-7D described below. In one example, a patient will select a virtual reality substance abuse treatment simulation from an array of virtual reality substance abuse treatment simulations that have been customized for that patient. In another example, the healthcare professional may select a patient from a list of available patients and then select a virtual reality substance abuse treatment simulation associated with that patient.

At 504, instructions for running the virtual reality substance abuse treatment simulation are executed. The instruction may be executed on the virtual reality headset 106 of FIG. 1. Alternatively, the instructions may be executed on the computing device 102 of FIG. 1 that is in communication with the virtual reality headset 106. At 506, the virtual reality substance abuse treatment simulation is rendered for display to the patient. For example, a patient may select the desired virtual reality substance abuse treatment simulation as described above while wearing the virtual reality headset causing the virtual reality substance abuse treatment simulation to render.

At 508, stimuli content associated with the type of substance and one or more triggers are displayed. The stimuli content may be facsimiles of any object that a patient associates with the type of substance such as but not limited to beer bottles, a pipe, a bong, needles, or the like. The image assets associated with the stimuli content may be stored within the content library 310 whereas the placement details of how and where content is located within the virtual reality substance abuse treatment simulation may be stored in the simulation data store 308, the patient configurations data store 306, or a combination of both.

At 510, the data indicative of exposures of the patient to ones of the stimuli content is received. The data may be received by the remote device 114 of FIG. 1. The remote device may then communicate this data to the virtual reality headset 106, for real-time display to the patient, or the computing device 102 of FIG. 1. The data may also be transmitted to the software platform 300 using the interface software 302. The interface software may then communicate the data to the customization software 304. The customization software 304 may store the data in the simulation data store 308 associated with the patient and virtual reality substance abuse treatment simulation. The recommendation software 312 may then use the data to make recommendations regarding the experience of the patient during the virtual reality substance abuse treatment simulation. The recommendation software 312 may use a machine learning module to analyze the data and determine if the virtual reality substance abuse treatment simulation should be further customized to provide an optimal experience for the patient.

Figure 6A:
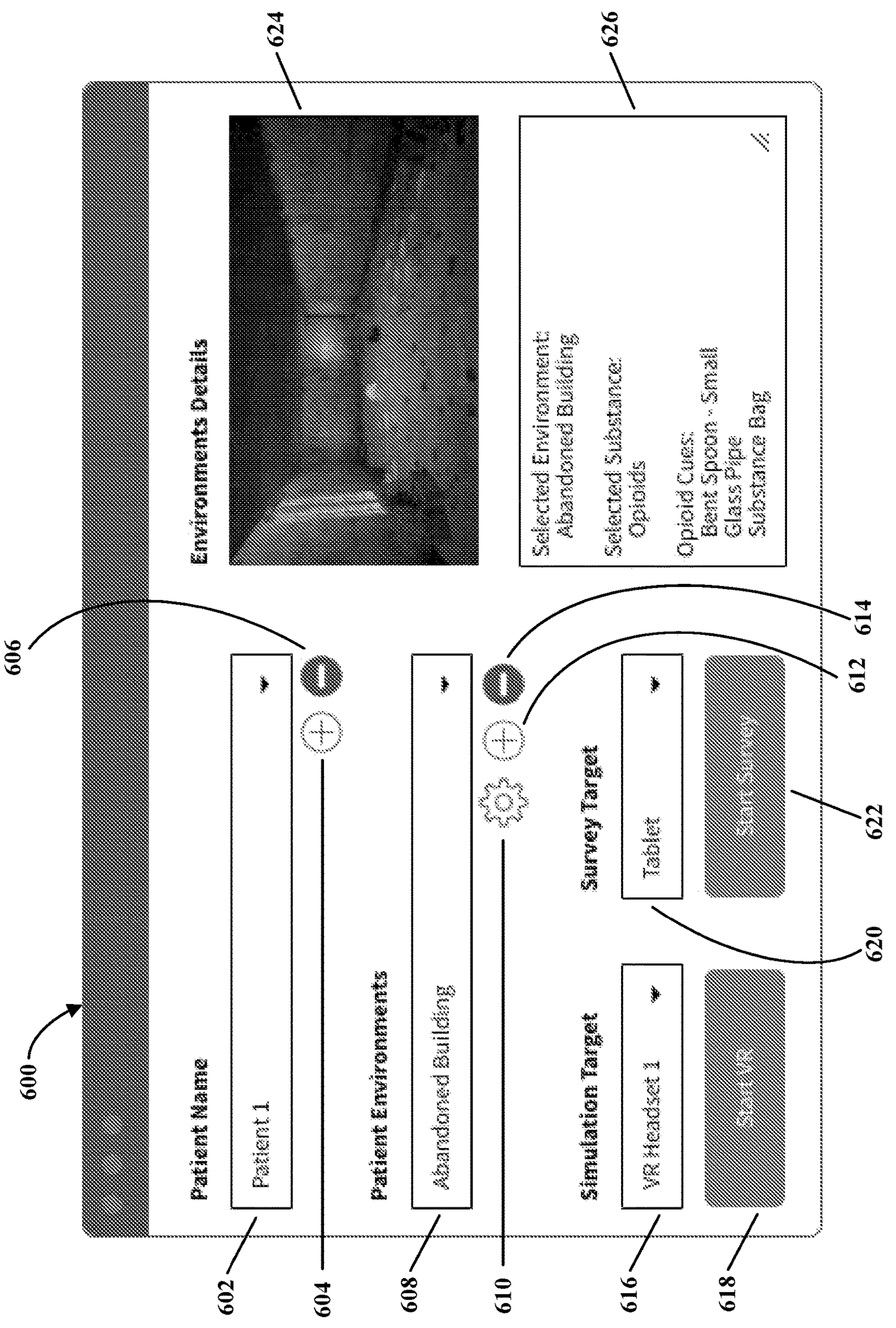
FIGS. 6A-6E are illustrations of graphical user interfaces (GUIs) for creating and customizing a virtual reality substance abuse treatment simulation from a computing device.

FIGS. 6A-6E are illustrations of GUIs for creating and customizing a virtual reality substance abuse treatment simulation from the computing device 102 and/or the remote device 114. FIG. 6A is an illustration of a GUI 600 for managing virtual environments associated with a patient according to implementations of this disclosure. The patient name dropdown list 602 may be populated by output 316 received from the interface software 302 of the software platform 300. A user can select a patient from the patient name dropdown list 602 or alternatively the patient can add a new patient to the patient name dropdown list using the patient add button 604. If the patient adds a new patient name to the patient name dropdown list 602, the patient name may be sent as input 314 to the interface software 302 of the software platform 300. The patient name may be used by the customization software 304 and stored in the simulation data store 308. Additionally, a user may remove a patient name from the patient name dropdown list 602 using the delete patient button 606. The delete patient button may send input 314 to the interface software 302 which may route through the customization software 304 to remove the patient name, as well as associated data and configurations from the simulation data store 308 and the patient configurations data store 306.

After a user selects a patient name from the patent name dropdown list 602, the virtual environments, associated with that patient, may be populated in the virtual environments dropdown list 608. A user may select a virtual environment from the virtual environment dropdown list 608. A user may also add a new virtual environment by pressing the new virtual environment button 612. A new virtual environment may be added using the interfaces described below for FIGS.

6B-6E. Alternatively a user may delete a virtual environment using the delete virtual environment button 614. The delete virtual environment button 614 may send input 314 to the interface software 302 which may route through the customization software 304 to remove the virtual environment. Removing the virtual environment may cause all data in the simulation data store 308 and the patient configurations data store 306 related to the virtual environment to be deleted. Additionally, the configure virtual environment button 610 may cause FIG. 6B to be displayed. After a virtual environment has been selected from the virtual environment dropdown 608, a substance abuse virtual reality treatment simulation can be started using the start VR button 618. A user may cause the simulation instructions 108 to be executed which may cause the rendering of the virtual reality substance abuse treatment simulation to be displayed on various devices by selecting a device from the simulation target dropdown list 616. The simulation target may be any computing device 102 or virtual reality headset 106. Additionally, after a virtual environment is selected from the virtual environment dropdown list 608 a user can start a survey using the start survey button 622. The survey may be started on a target device by selecting a target from the survey target dropdown list 620. The target device may be any computing device 102 or remote device 114.

Furthermore, the details of the selected virtual environment may be displayed under the heading of Environment Details. The graphical representation of the virtual environment may be displayed in the environment image 624. The environment image 624 may be output 316 from the interface software 302. The software interface 302 may pull the environment image 624 out of the content library 310 through the customization software 304. The environment details description 626 may also be displayed describing the details of the customizations within the virtual reality substance abuse treatment simulation. The details may contain information contained in the simulation data store 308, the patient configurations data store 306, the content library 310, or a combination thereof. For example, the details may contain the name of the selected environment such Abandoned Building, the type of substance indicated such as but not limited to Opioids, the stimuli content such as Bent Spoon-Small, Glass Pipe, or Substance Bag or any combination thereof.

Figure 6B:
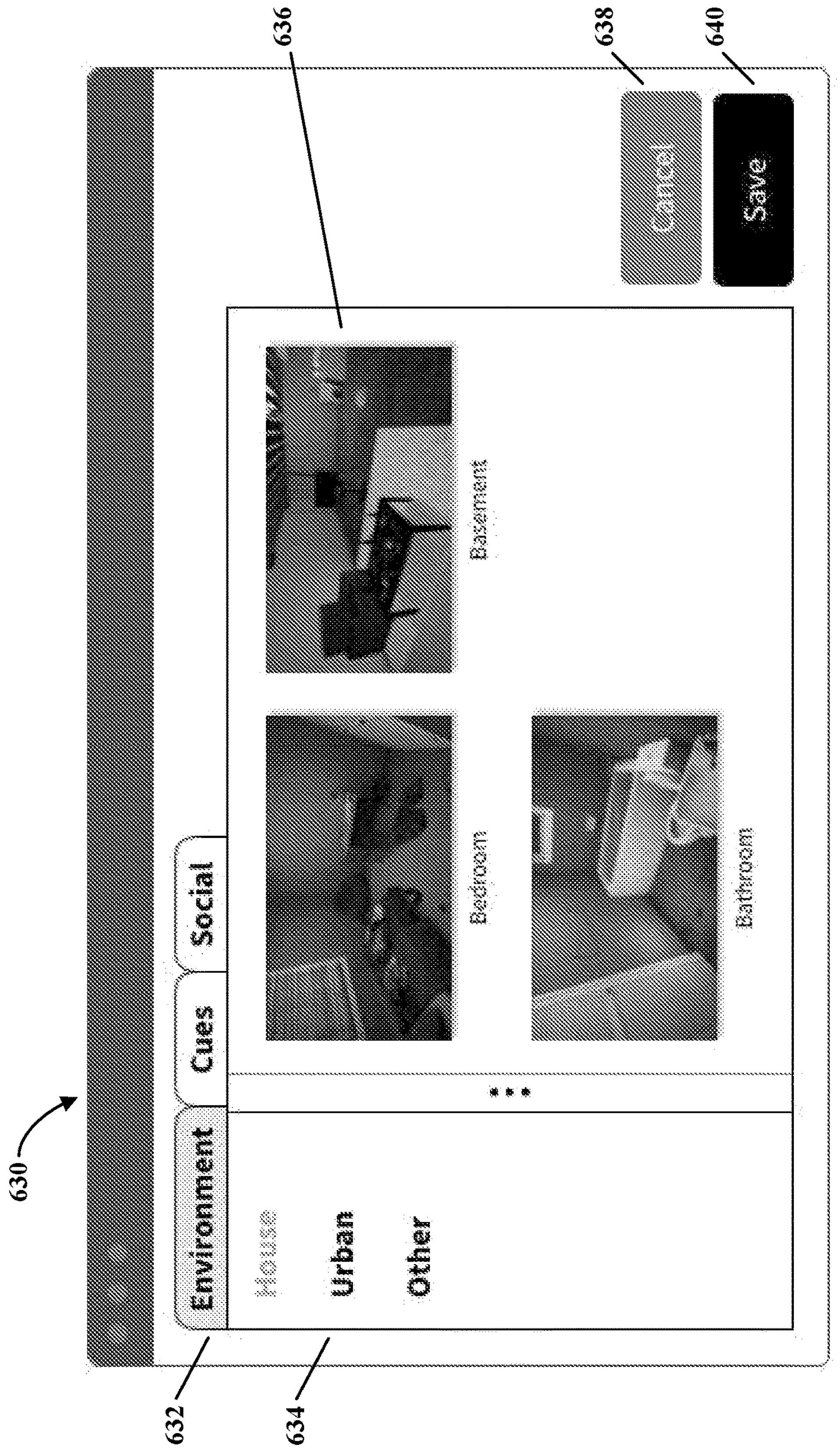

As indicated above, selecting the new virtual environment button 612 or configure virtual environment button 610 may cause the FIG. 6B to be displayed. FIG. 6B is an illustration of a GUI 630 for customizing a virtual environment. Specifically, the GUI 630 is provided for customizing the areas of the virtual reality substance abuse treatment simulation. The environment tab 632 is selected, indicating that the areas of the environment can be customized using this interface. The area category selection list 634 may allow a user to filter the type of area for selection. The area selection images 636, display the areas matching the selected type of area from the area category selection list 634. The area category selections and the corresponding areas for each category may be output 316 from the interface software 302. The interface software may retrieve the categories and corresponding areas from the content library 310 through the customization software 304. For example, the content library may have one or more area categories such as House, Urban, Other, or any other category name. Each category may have one or more areas associated with it such as but not limited to Bedroom, Basement. Bathroom as depicted in the area selection images 636. Using this interface, a user may select the areas to be displayed within the virtual reality substance abuse treatment simulation.

A user may exit this interface by selecting the cancel button 638 or alternatively a user may save the selected information using the save button 640. Selecting the cancel button 638 may cause the GUI 630 to close and return back to the GUI 600. Selecting the save button 640 may cause the selected areas to be sent as input 314 to the interface software 302. The interface software may transmit the input 314 to the customization software 304. The customization software 304 may cause the received input 314 to be stored in the simulation data store 308, the patient configurations data store 306, or both.

Figure 6C:
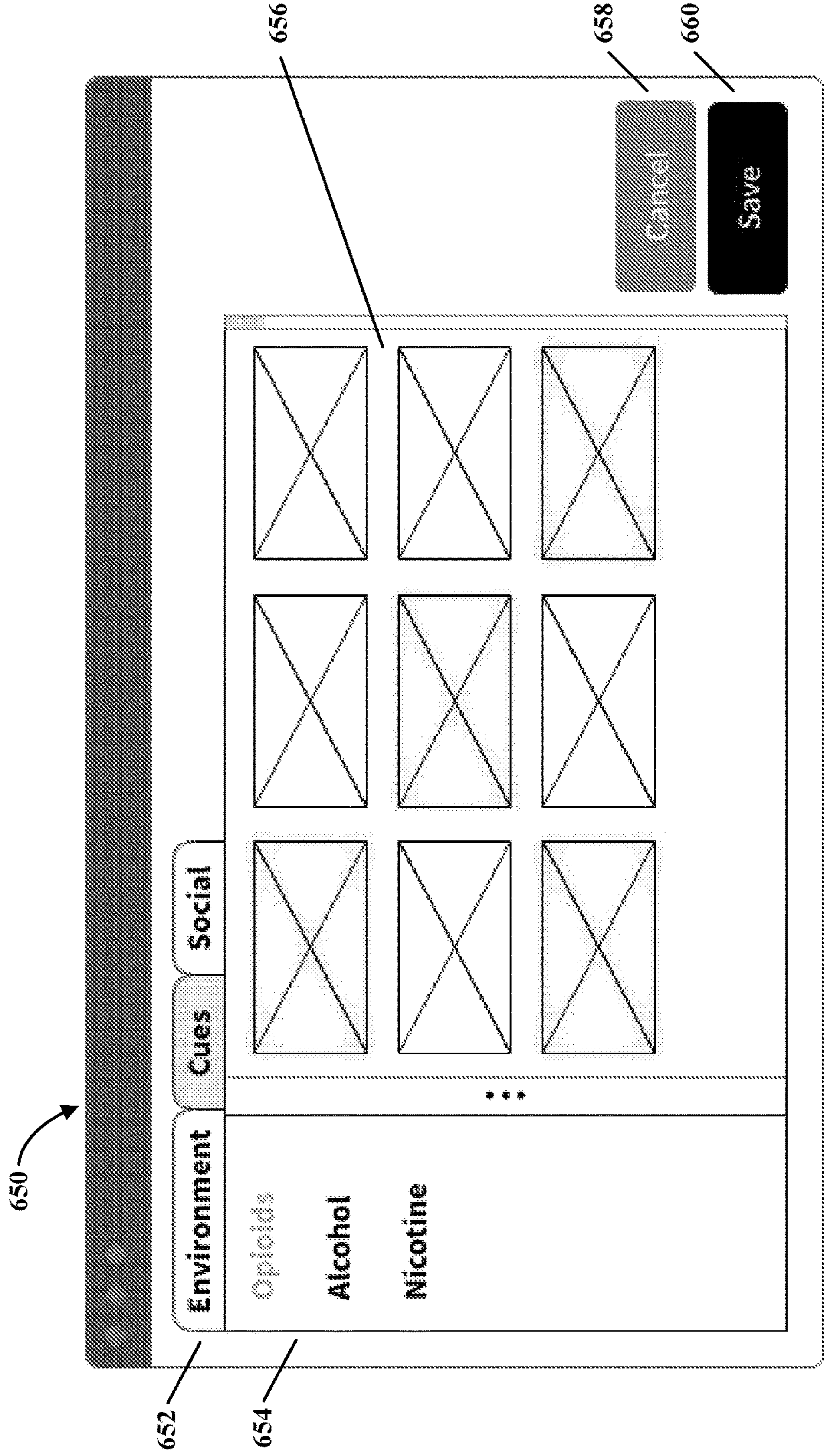

FIG. 6C is an illustration of a GUI 650 for selecting content stimuli to be rendered within the virtual reality substance abuse treatment simulation. The GUI 650 can be accessed by selecting the cues tab 652. Selecting the cues tab 652 may cause the substance category list 654 to be populated. The substance category list 654 may be populated by output 316 from the interface software 302. The interface software 302 may retrieve the substance categories from the simulation data store 308, the content library 310, or both. The stimuli content images 656 are displayed based on the selected substance category 654. A user may select one or more stimuli content from the stimuli content images 656 from one or more substance categories.

The user may save the selected stimuli content using the save button 660. The save button 660 may cause the stimuli content to be sent to the interface software 302 as input 314. The interface software may pass the input 314 to the customization software 304. The customization software 304 may cause the input 314 to be saved as stimuli content associated with the virtual environment in the simulation data store 308 and the patient configurations data store 306. A user may exit this interface by pressing the cancel button 658. Pressing the cancel button 658 may cause the GUI 650 to close and return back to the GUI 600.

Figure 6D:
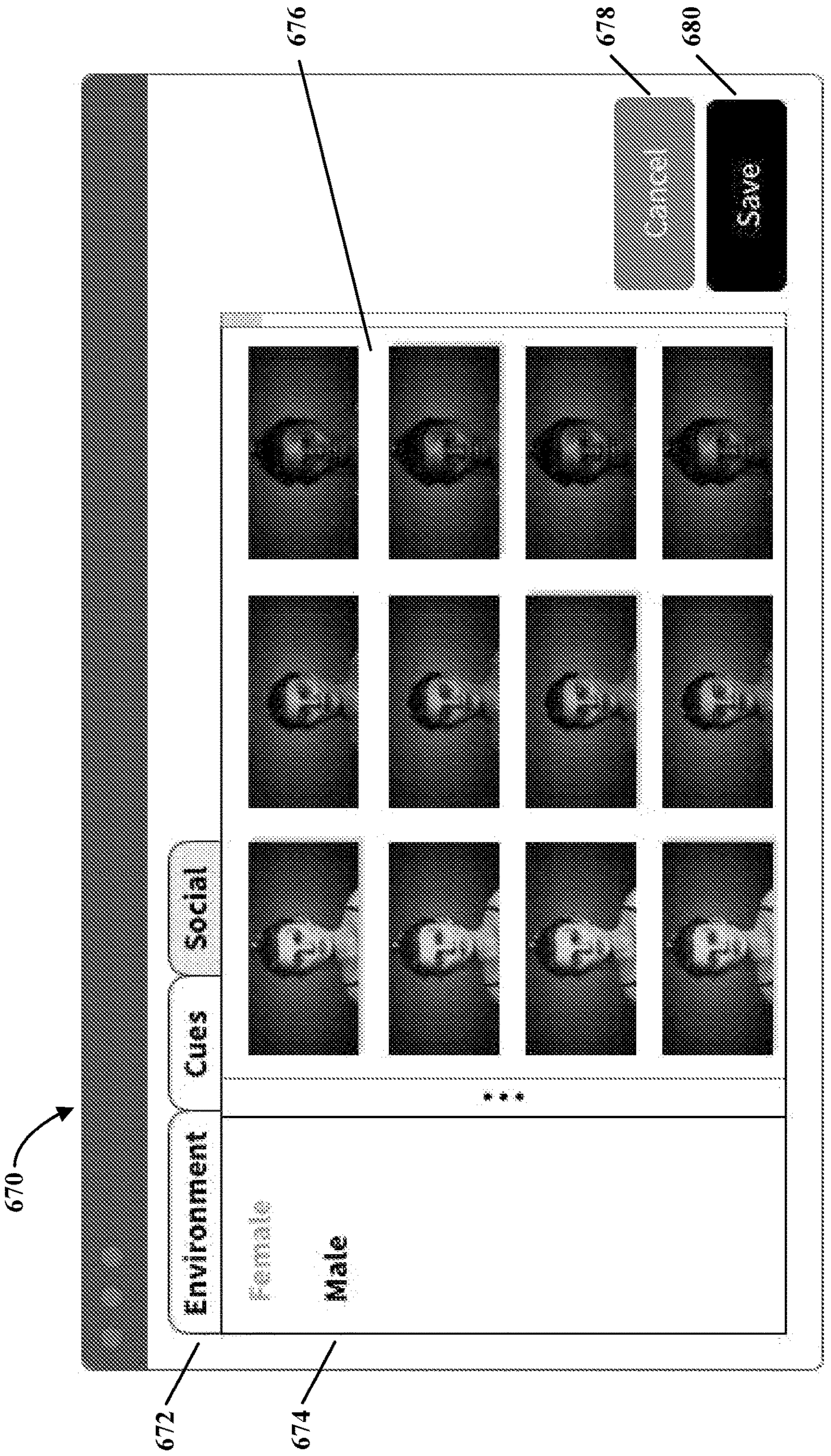

FIG. 6D is an illustration of a GUI 670 for selecting social cues to be rendered within the virtual reality substance abuse treatment simulation. Selecting the social tab 672 may cause the avatar type list 674 to be populated. The avatar type list 674 may be populated by output 316 from the interface software 302. The interface software 302 may retrieve the avatar types from the simulation data store 308, the content library 310 or both. The avatar images 676 are displayed based on the selected avatar type. For example, a user may select the female avatar type from the avatar type list 674 causing the avatar images 676 to be populated with images depicting female avatars that may be selected.

A user may select one or more avatar images from the avatar images 676 from one or more avatar types. The user may save the selected avatar images using the save button 680. The save button 680 may cause the avatar images to be sent to the interface software 302 as input 314. The interface software may pass the input 314 to the customization software 304. The customization software 304 may cause the input 314 to be saved as avatar images associated with the virtual environment in the simulation data store 308 and the patient configurations data store 306. A user may exit the GUI 670 by pressing the cancel button 678. Pressing the cancel button 678 may cause the GUI 670 to close and return back to the GUI 600.

Figure 6E:
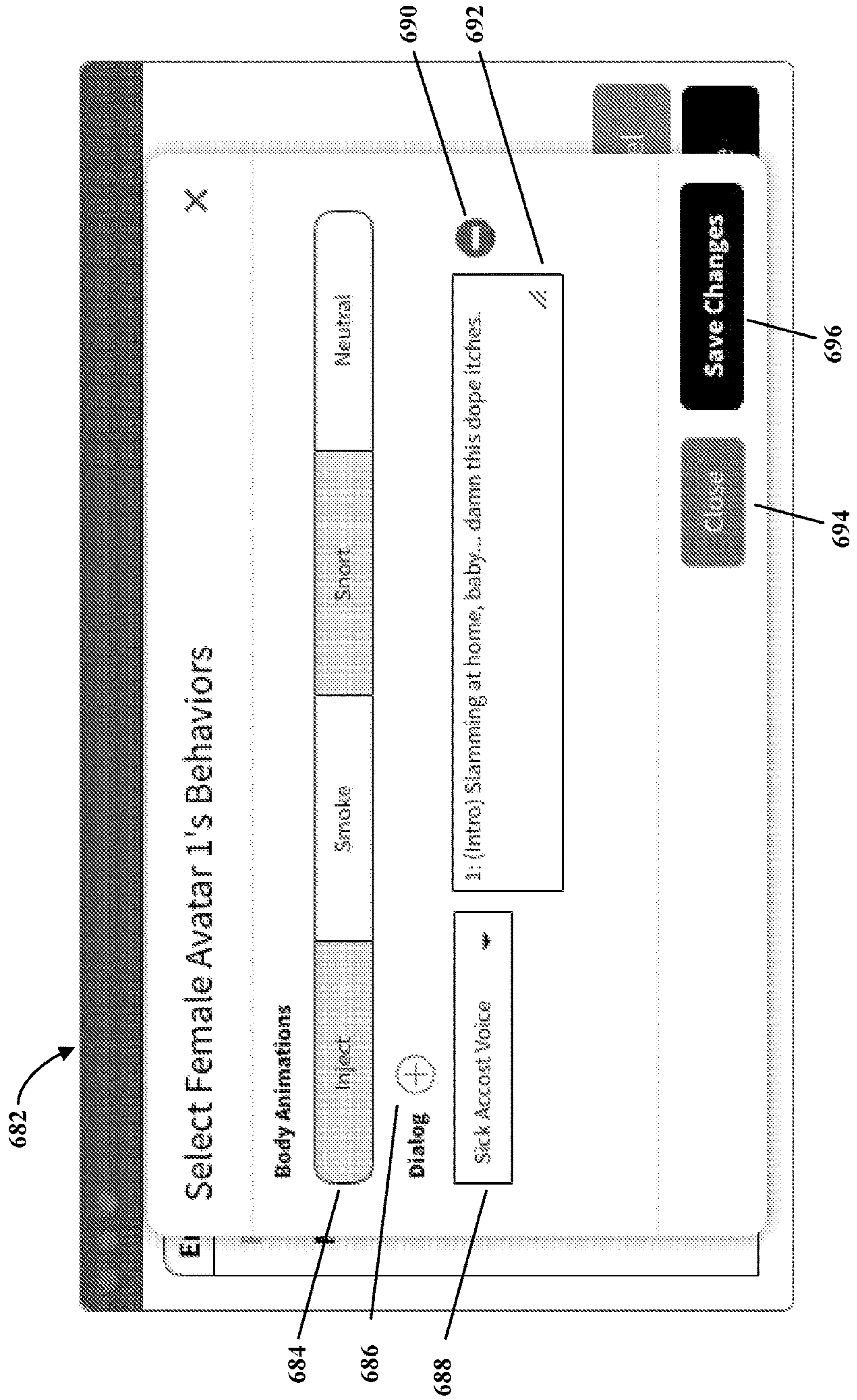

FIG. 6E is an illustration of a GUI 682 for configuring a selected avatars behaviors within the substance abuse virtual reality treatment simulation. A user can associate different interactions with an avatar using the body animations selection buttons 684. Using the body animation selection buttons 684 a user can associate one or more actions to an avatar. For example, a user could assign any of the following but not limited to inject, smoke, snort, neutral animations, or the like, or any combination thereof to an avatar for rendering during a substance abuse virtual reality treatment simulation. A user can also assign different dialog options to an avatar using the GUI 682. A user may use the add dialog button 686 to create a new dialog option for an avatar. An avatar may have no dialog options associated with it or an avatar may have one or more dialog options associated with it.

A user can assign a dialog voice type for each dialog option using the dialog voice type dropdown list 688. Additionally, a user can enter dialog text for each dialog option added using the dialog textbox 692. Using the remove dialog option button 690 a user can remove (e.g., disable) an associated dialog option from an avatar. The user may save the associated avatar behaviors using the save changes button 696. The save changes button 696 may cause the avatar behaviors to be sent to the interface software 302 as input 314. The interface software may pass the input 314 to the customization software 304. The customization software 304 may cause the input 314 to be saved as avatar behaviors associated with the virtual environment in the simulation data store 308 and the patient configurations data store 306. A user may exit this interface by pressing the cancel button 694. Pressing the cancel button 694 may cause the GUI 682 to close and return back to the GUI 670.

Figure 7A:
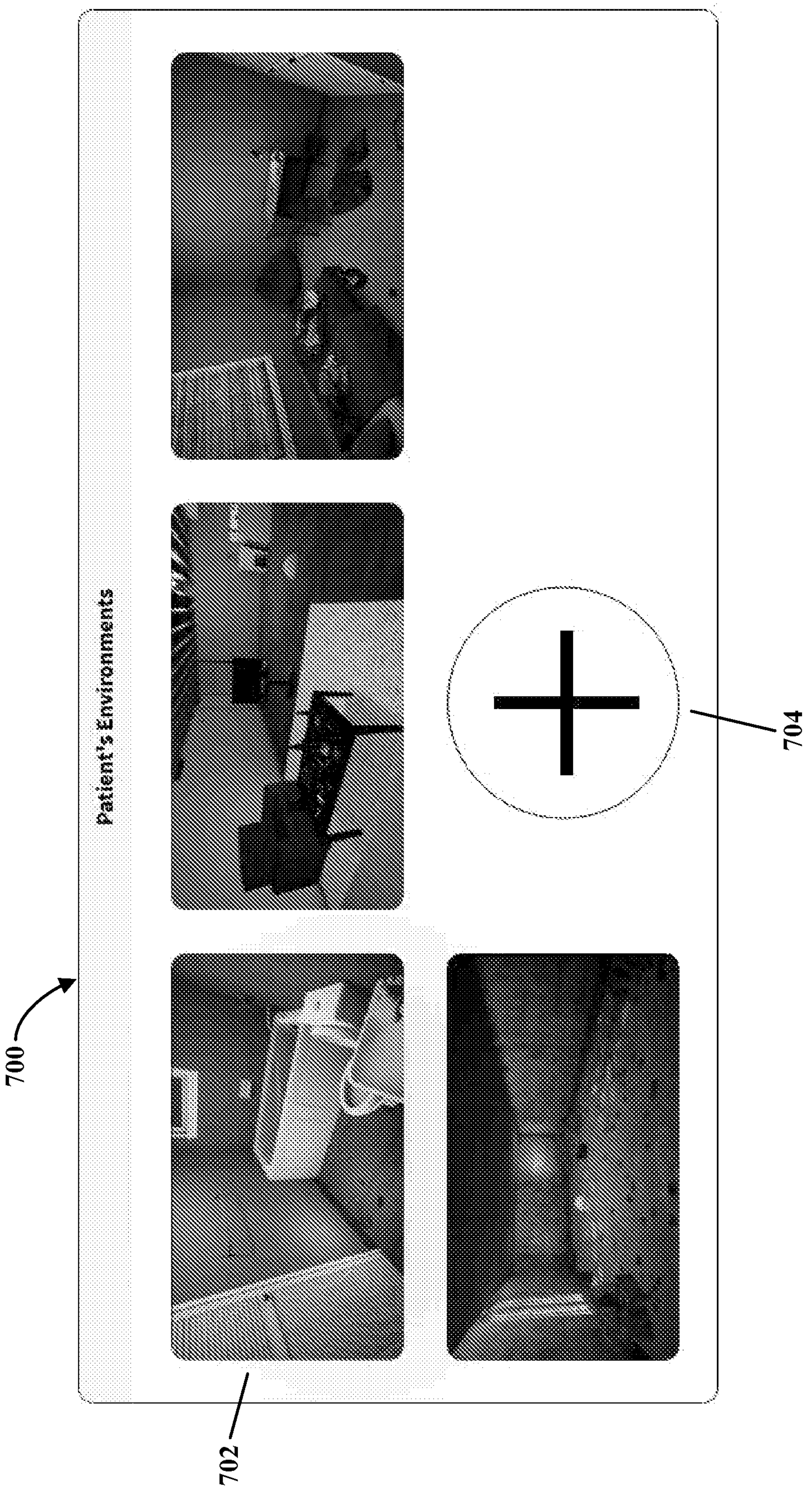
FIGS. 7A-7D are illustrations of GUIs for creating and customizing a virtual reality substance abuse treatment simulation from a virtual reality headset.

FIGS. 7A-7D are illustrations of GUIs for creating and customizing a virtual reality substance abuse treatment simulation from a virtual reality headset. FIG. 7A is an illustration of a GUI 700 for a virtual reality headset for viewing and configuring a substance abuse virtual reality treatment simulation. A user may see all the available virtual environments for the configured patient using the virtual environment view 702. A user may select a virtual environment to customize further or render on the virtual reality headset. Selecting a virtual environment for customization may cause the GUI 710 of FIG. 7B (described below) to be rendered. Alternatively, a user can add a new virtual environment using the add environment button 704. Pressing the add environment button 704 may cause the GUI 710 of FIG. 7B to be rendered.

Figure 7B:
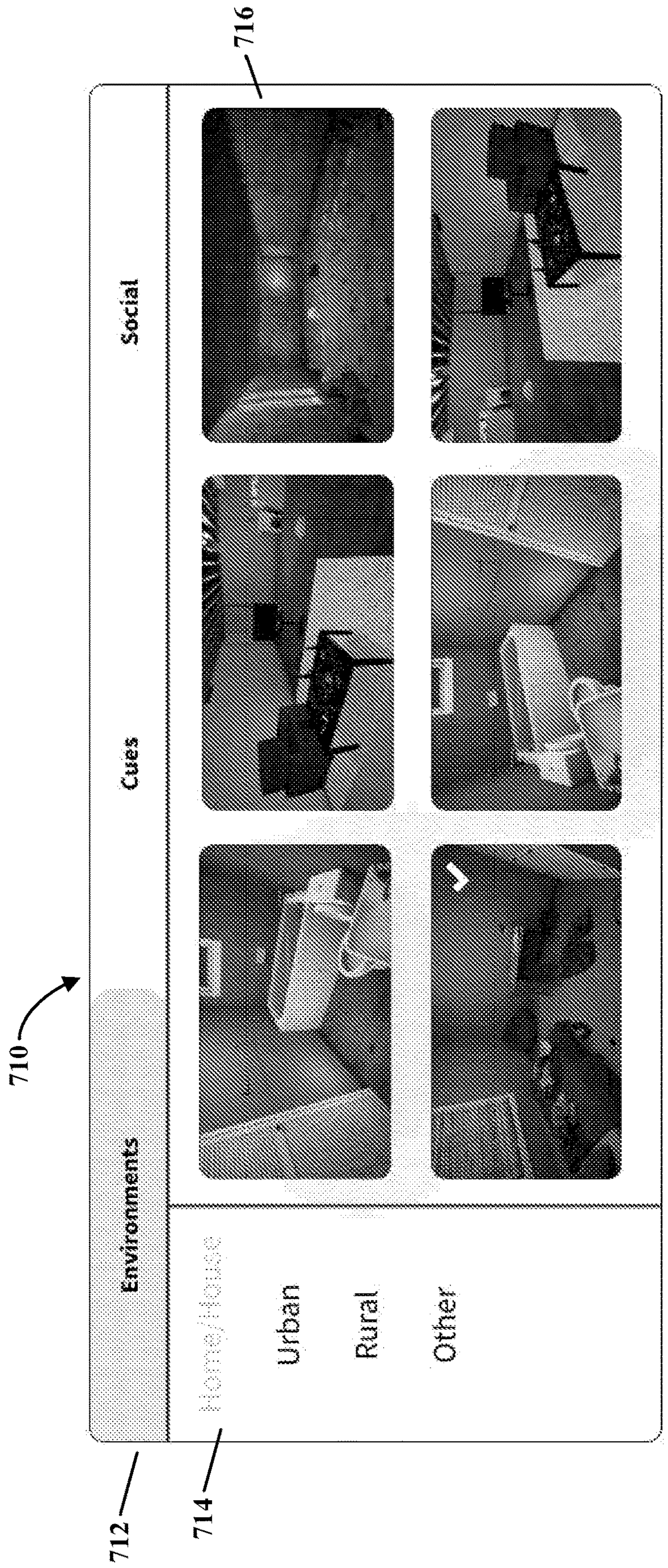

FIG. 7B is an illustration of a GUI 710 for customizing the selected areas within a virtual environment. The section selection button 712 may indicate what aspect of the virtual environment that the user is customizing. For example, selecting the Environment option indicates that the user will be able to customize the environments within the new environment. The area category selection list 714 is similar to the area category selection list 634 of FIG. 6B and may function in a substantially similar way. Selecting an area category from the area category selection list 714 may cause the area selection images 716 to be displayed for the corresponding area category. The area selection images 716 are similar to the area selection images 636 or FIG. 6B and may function in a substantially similar way.

Figure 7C:
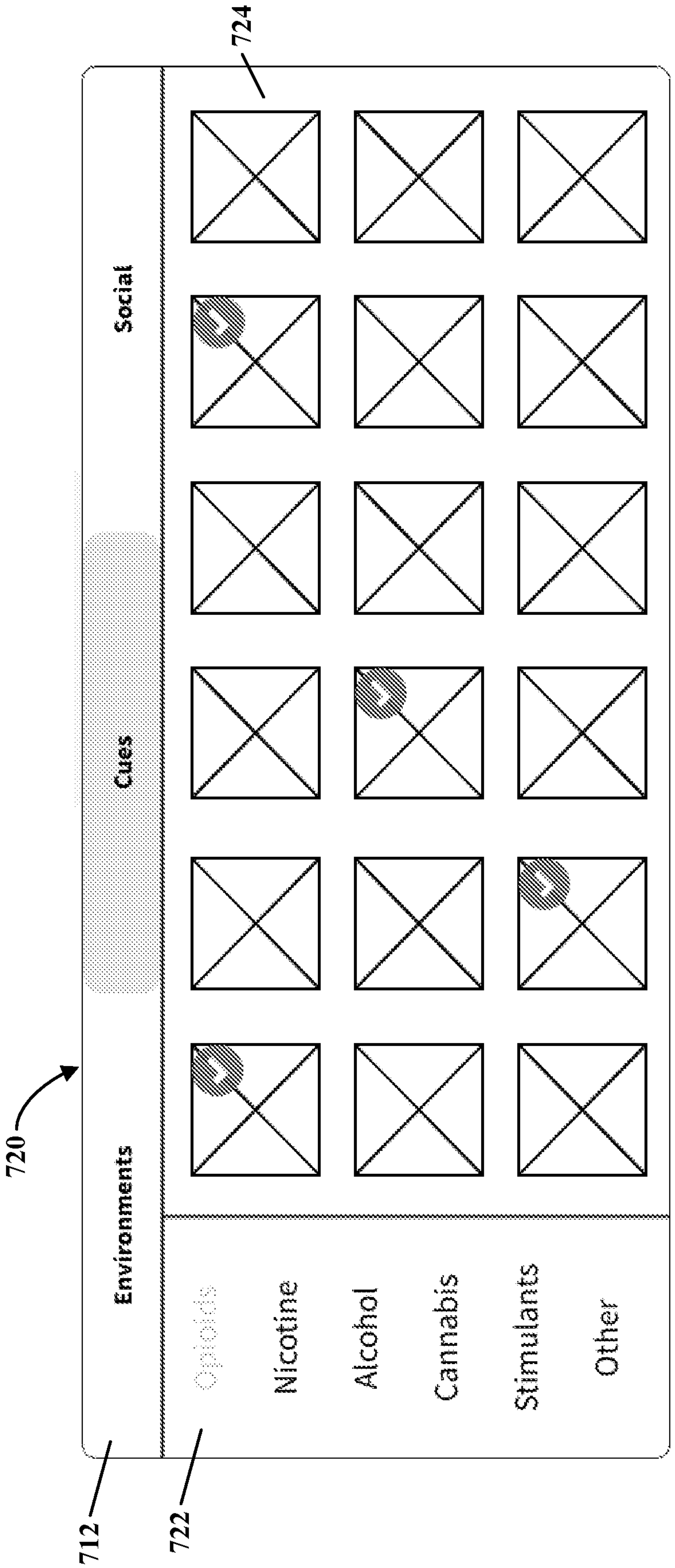

FIG. 7C is an illustration of a GUI 720 for customizing the stimuli content to be placed within the virtual environment. The GUI 720 may be displayed by selecting the Cues option on the section selection button 712. When the Cues option is selected on the section selection button 712 the substance category list 722 may be populated. The substance category list 722 may be similar to the substance category list 654 of FIG. 6C and function is a substantially similar way as described above. Selecting a substance category from the substance category list 722 may cause the associated stimuli content images 724 to be displayed. The stimuli content images 724 may be similar to the stimuli content images 656 of FIG. 6C and function in a substantially similar way as described above.

Figure 7D:
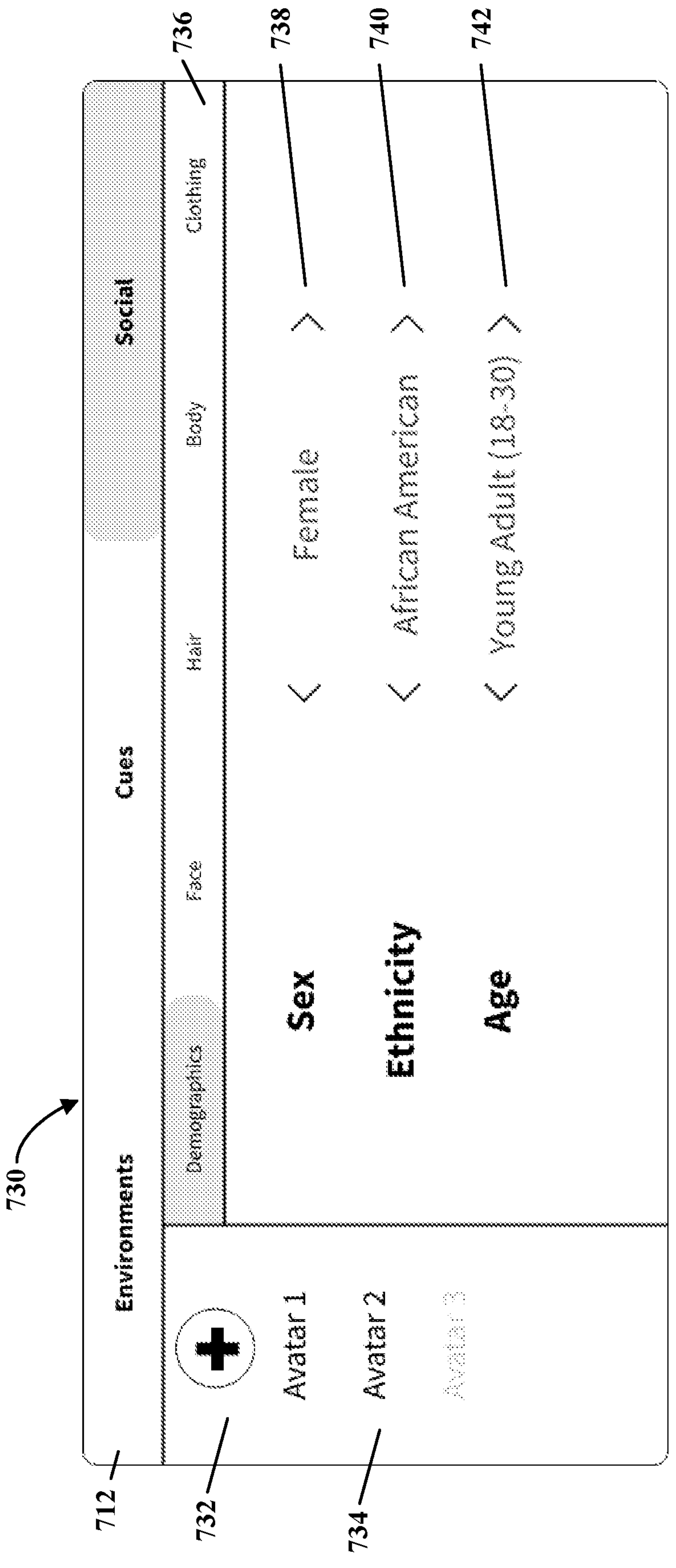

FIG. 7D is an illustration of a GUI 730 for customizing the avatars that may be placed within the virtual environment. The GUI 730 may be displayed when a user selects the Social option on the section selection button 712. Selecting the Social option on the section selection button 712 may cause the avatar type list 734 to be populated. The avatar type list 734 may be populated by output 316 from the interface software 302. The interface software 302 may retrieve the avatar types from the simulation data store 308, the content library 310, or a combination thereof. Additionally, the add avatar button 732 may allow a user to add more avatar to the avatar type list 734. Selecting an avatar from the avatar type list 734 may allow a user to customize the selected avatar. A user may be able to customize details about the avatar including but not limited to demographics, face, hair, body, clothing, or the like. A user can select which area of the avatar to customize by selecting an option from the avatar customization section list 736. For example, the user may select demographics from the avatar customization section list 736 which may cause the following attributes to be displayed for customization, Sex 738, Ethnicity 749, or Age 742. The illustrated attributes are just demonstrative of the types of attributes that can be display; however, other implementations are not limited to these attributes.

Figure 8:
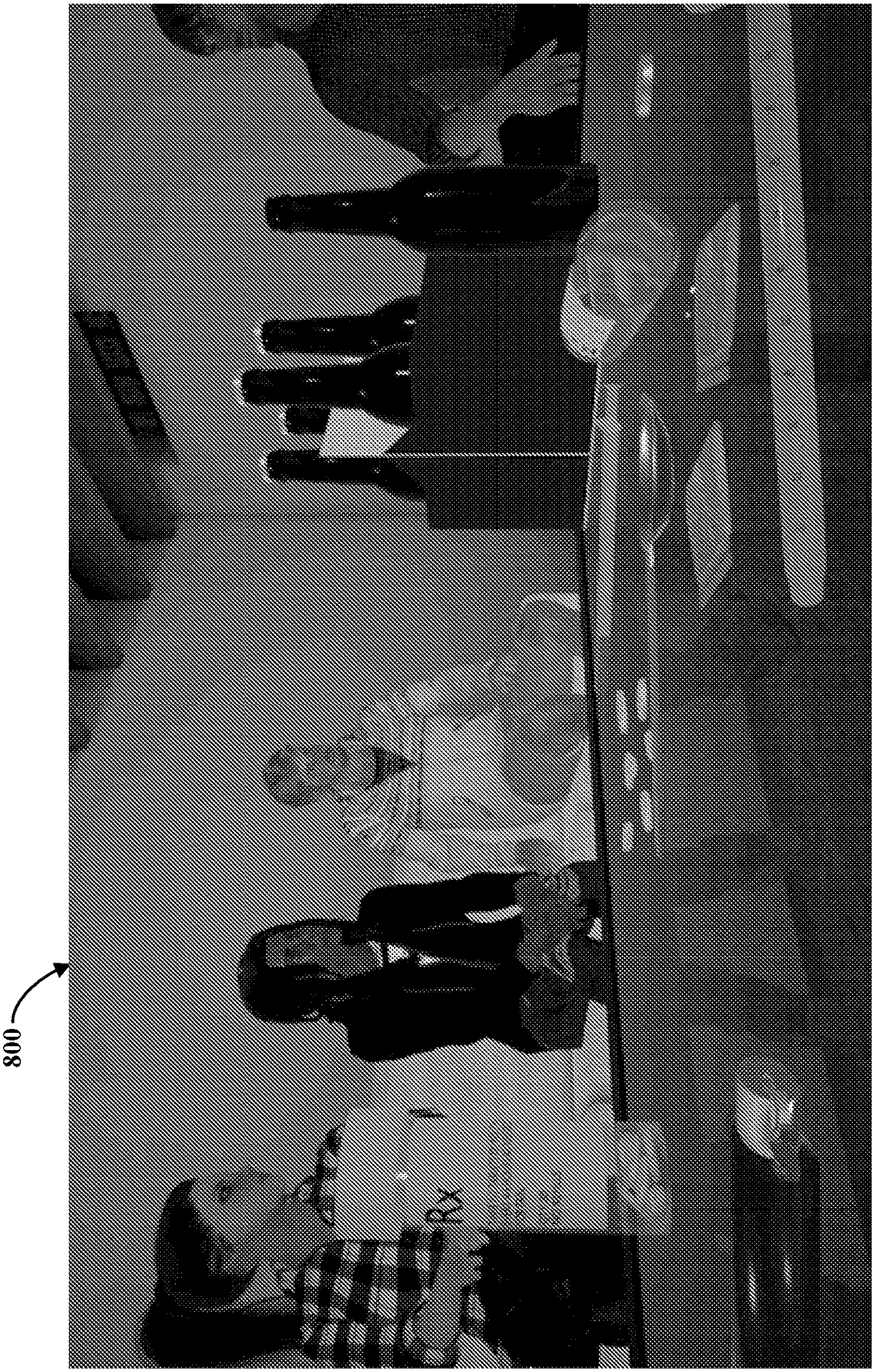
FIG. 8 is an illustration of example output rendered within a substance abuse virtual reality treatment simulation.

FIG. 8 is an illustration of an example render 800 representing output rendered within a substance abuse virtual reality treatment simulation, as may be viewed via a computing device 102 or a virtual reality headset 106. The render 800 depicts a virtual environment with an area containing several other elements. The area may be a basement as displayed or any other area available within the content library 310. The render 800 also depicts several avatars. The avatars may be selected based on their familiarity to the patient or they may be randomly generated. Additionally, the render displays several stimuli content, such as pills, needles, beer bottles, prescription drugs. The stimuli content may be any other stimuli content from the content library 310.

The implementations of this disclosure can be described in terms of functional block components and various processing operations. Such functional block components can be realized by a number of hardware or software components that perform the specified functions. For example, the disclosed implementations can employ various integrated circuit components (e.g., memory elements, processing elements, logic elements, look-up tables, and the like), which can carry out a variety of functions under the control of one or more microprocessors or other control devices. Similarly, where the elements of the disclosed implementations are implemented using software programming or software elements, the systems and techniques can be implemented with a programming or scripting language, such as C, C++, Java, JavaScript, assembler, or the like, with the various algorithms being implemented with a combination of data structures, objects, processes, routines, or other programming elements.

Functional aspects can be implemented in algorithms that execute on one or more processors. Furthermore, the implementations of the systems and techniques disclosed herein could employ a number of conventional techniques for electronics configuration, signal processing or control, data processing, and the like. The words “mechanism” and “component” are used broadly and are not limited to mechanical or physical implementations, but can include software routines in conjunction with processors, etc. Likewise, the terms "system" or "tool" as used herein and in the figures, but in any event based on their context, may be understood as corresponding to a functional unit implemented using software, hardware (e.g., an integrated circuit, such as an ASIC), or a combination of software and hardware. In certain contexts, such systems or mechanisms may be understood to be a processor-implemented software system or processor-implemented software mechanism that is part of or callable by an executable program, which may itself be wholly or partly composed of such linked systems or mechanisms.

Implementations or portions of implementations of the above disclosure can take the form of a computer program product accessible from, for example, a computer-usable or computer-readable medium. A computer-usable or computer-readable medium can be a device that can, for example, tangibly contain, store, communicate, or transport a program or data structure for use by or in connection with a processor. The medium can be, for example, an electronic, magnetic, optical, electromagnetic, or semiconductor device. Other suitable mediums are also available. Such computer-usable or computer-readable media can be referred to as non-transitory memory or media, and can include volatile memory or non-volatile memory that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method, comprising:

receiving input specific to a patient, the input including a type of substance used by the patient, one or more triggers for inducing substance use by the patient and one or more virtual areas associated with prior use of the type of substance by the patient, wherein a virtual area of the one or more virtual areas is a representation of a physical location and the one or more virtual areas are selected by at least one of the patient or a healthcare professional associated with the patient;

generating, using the input, a virtual reality substance abuse treatment simulation prior to execution of the virtual reality substance abuse treatment simulation, wherein generating the virtual reality substance abuse treatment simulation includes generating a virtual environment including the one or more virtual areas and virtual representations of the one or more triggers;

executing, in response to generating the virtual reality substance abuse treatment simulation, at a computing device with which a virtual reality headset worn by the patient is in communication, instructions for running the virtual reality substance abuse treatment simulation to cause, for display at the virtual reality headset, a rendering of the virtual environment including the one or more virtual areas, and a rendering of stimuli content associated with the type of substance within at least one of the one or more virtual areas of the virtual environment;

transmitting, to a remote device, data indicative of exposures of the patient to ones of the stimuli content within respective ones of the virtual areas during the virtual reality substance abuse treatment simulation; and modifying, based on a change from a software user interface, at least one of the stimuli content during the virtual reality substance abuse treatment simulation, wherein the change is based on the data indicative of exposures of the patient and includes at least one of enabling, disabling, or adjusting an intensity of the at least one of the stimuli content.

2. The method of claim 1, wherein generating the virtual reality substance abuse treatment simulation comprises:

selecting the stimuli content from a content library according to the input; and determining positions for the stimuli content within an environment for the virtual reality substance abuse treatment simulation according to the input.

3. The method of claim 2, wherein the environment includes the one or more virtual areas and the one or more virtual areas are selected based on one or both of a substance abuse history or a trauma history of the patient.

4. The method of claim 3, wherein at least one of the one or more virtual areas is automatically generated using a machine learning model according to the input.

5. The method of claim 1, wherein the data indicates physiological reactions by the patient to ones of the stimuli content.

6. The method of claim 5, wherein the data is collected using one or more biometric sensors in communication with the virtual reality headset.

7. The method of claim 1, wherein the data is output for display at the remote device in real-time with respective ones of the exposures during the virtual reality substance abuse treatment simulation.

8. The method of claim 1, wherein the data indicates one or more recommended updates to the virtual reality substance abuse treatment simulation to further a course of substance abuse treatment for the patient.

9. The method of claim 8, comprising:

automatically updating the virtual reality substance abuse treatment simulation according to the data to cause a change to at least one of the stimuli content.

10. The method of claim 1, wherein the remote device is associated with one of the patient or the healthcare professional associated with the patient.

11. A device comprising:

a memory; and a processor, the processor configured to execute instructions stored in memory to:

receive input specific to a patient, the input including a type of substance used by the patient, one or more triggers for inducing substance use by the patient and one or more virtual areas associated with prior use of the type of substance by the patient, wherein a virtual area of the one or more virtual areas is a representation of a physical location and the one or more virtual areas are selected by at least one of the patient or a healthcare professional associated with the patient;

generate, using the input, a virtual reality substance abuse treatment simulation specific to the patient prior to execution of the virtual reality substance abuse treatment simulation, wherein to generate the virtual reality substance abuse treatment simulation includes to generate a virtual environment including the one or more virtual areas and virtual representations of the one or more triggers;

execute, in response to the generation of the virtual reality substance abuse treatment simulation, instructions for running the virtual reality substance abuse treatment simulation to cause, for display at a virtual reality headset, a rendering of the virtual environment including the one or more virtual areas, and a rendering of stimuli content associated with a type of substance within at least one of the one or more virtual areas of the virtual environment;

output data indicative of exposures of the patient to ones of the stimuli content within respective ones of the virtual areas during the virtual reality substance abuse treatment simulation; and modify, based on a change from a software user interface, at least one of the stimuli content during the virtual reality substance abuse treatment simulation, wherein the change is based on the data indicative of exposures of the patient and includes at least one of enabling, disabling, or adjusting an intensity of the at least one of the stimuli content.

12. The device of claim 11, wherein the device is the virtual reality headset worn by the patient.

13. The device of claim 12, wherein the processor is further configured to execute the instructions to:

receive an update to the virtual reality substance abuse treatment simulation according to the data indicative of exposures of the patient that causes a change to ones of the stimuli content.

14. The device of claim 11, wherein the stimuli content is rendered within an environment including the one or more virtual areas.

15. The device of claim 14, wherein the one or more virtual areas are selected, from a content library, based on one or both of a substance abuse history or a trauma history of the patient.

16. A system comprising:

a remote device for receiving data indicative of exposures of a patient to one or more stimuli content within a respective virtual area of one or more virtual areas during a virtual reality substance abuse treatment simulation and input usable to generate the virtual reality substance abuse treatment simulation, wherein the input is specific to the patient and includes a type of substance used by the patient, one or more triggers for inducing substance use by the patient and the one or more virtual areas associated with prior use of the type of substance by the patient and, wherein a virtual area of the one or more virtual areas is a representation of a physical location and the one or more virtual areas are selected by at least one of the patient or a healthcare professional associated with the patient;

a computing device, in communication with the remote device, for generating, using the input, the virtual reality substance abuse treatment simulation prior to execution of the virtual reality substance abuse treatment simulation, wherein to generate the virtual reality substance abuse treatment simulation includes to generate a virtual environment including the one or more virtual areas and virtual representations of the one or more triggers, wherein the computing device is configured to modify, based on a change from a software user interface, at least one of the stimuli content of the virtual reality substance abuse treatment simulation, wherein the change is based on the data indicative of exposures of the patient and includes at least one of enabling, disabling, or adjusting an intensity of the at least one of the stimuli content; and a virtual reality headset, in communication with the computing device, for rendering the virtual environment including the one or more virtual areas, and the one or more stimuli content associated with the type of substance within at least one of the one or more virtual areas.

17. The system of claim 16, further comprising:

one or more biometrics sensors, in communication with the virtual reality headset, for collecting the data indicative of exposures of the patient.

18. The system of claim 17, wherein the data indicates physiological reactions by the patient to ones of the stimuli content.

19. The system of claim 16, wherein the input is collected using a questionnaire designed to solicit information about substance abuse history and trauma history of the patient.

20. The system of claim 19, wherein the one or more virtual areas are based on one or both of the substance abuse history or the trauma history of the patient.

* * * * *